US009073921B2

(12) United States Patent
Bruce et al.

(10) Patent No.: US 9,073,921 B2
(45) Date of Patent: Jul. 7, 2015

(54) SALT FORMS OF BICYCLIC HETEROCYCLIC DERIVATIVES

(71) Applicants: Ian Bruce, Billingshurst (GB); Sylvie Chamoin, Saint Louis (FR); Stephen Paul Collingwood, Haywards Heath (GB); Pascal Furet, Thann (GB); Vikki Furminger, Horsham (GB); Sarah Lewis, Horsham (GB); Jon Christopher Loren, San Diego, CA (US); Lin Lv, Shanghai (CN); Valentina Molten, San Diego, CA (US); Alex Michael Saunders, Leicester (GB); Duncan Shaw, Horsham (GB); Roy Maxwell Turner, London (GB); Vince Yeh, San Diego, CA (US)

(72) Inventors: Ian Bruce, Billingshurst (GB); Sylvie Chamoin, Saint Louis (FR); Stephen Paul Collingwood, Haywards Heath (GB); Pascal Furet, Thann (GB); Vikki Furminger, Horsham (GB); Sarah Lewis, Horsham (GB); Jon Christopher Loren, San Diego, CA (US); Lin Lv, Shanghai (CN); Valentina Molten, San Diego, CA (US); Alex Michael Saunders, Leicester (GB); Duncan Shaw, Horsham (GB); Roy Maxwell Turner, London (GB); Vince Yeh, San Diego, CA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/187,214

(22) Filed: Feb. 21, 2014

(65) Prior Publication Data
US 2014/0249177 A1 Sep. 4, 2014

(30) Foreign Application Priority Data

Mar. 1, 2013 (WO) ................ PCT/CN2013/072060

(51) Int. Cl.
| C07D 401/00 | (2006.01) |
| A61K 31/44 | (2006.01) |
| C07D 471/04 | (2006.01) |
| A61K 45/06 | (2006.01) |

(52) U.S. Cl.
CPC .............. *C07D 471/04* (2013.01); *A61K 45/06* (2013.01)

(58) Field of Classification Search
None
See application file for complete search history.

(56) References Cited

U.S. PATENT DOCUMENTS

| 2005/0054701 A1 | 3/2005 | Wallace et al. |
| 2007/0072862 A1 | 3/2007 | Dimauro et al. |
| 2013/0059846 A1 | 3/2013 | Yeh |

FOREIGN PATENT DOCUMENTS

| EP | 0 033 094 | 8/1981 |
| WO | 99/32477 | 7/1999 |
| WO | 00/07980 | 2/2000 |
| WO | 00/07991 | 2/2000 |
| WO | 00/55120 | 9/2000 |
| WO | 01/19788 | 3/2001 |
| WO | 01/27089 | 4/2001 |
| WO | 02/066477 | 8/2002 |
| WO | 02/066478 | 8/2002 |
| WO | 03/078435 | 9/2003 |
| WO | 2004/026867 | 4/2004 |
| WO | 2004/026872 | 4/2004 |
| WO | 2004/063330 | 7/2004 |
| WO | 2004/087646 | 10/2004 |
| WO | 2004/101563 | 11/2004 |
| WO | 2005/023759 | 3/2005 |
| WO | 2005/044797 | 5/2005 |
| WO | 2005/048953 | 6/2005 |
| WO | 2005/063739 | 7/2005 |
| WO | 2005/085227 | 9/2005 |
| WO | 2006/032342 | 3/2006 |
| WO | 2006/067445 | 6/2006 |
| WO | 2006/067446 | 6/2006 |
| WO | 2006/081172 | 8/2006 |
| WO | 2006/101455 | 9/2006 |
| WO | 2006/108640 | 10/2006 |
| WO | 2007/022380 | 2/2007 |
| WO | 2007/032936 | 3/2007 |
| WO | 2007/065664 | 6/2007 |
| WO | 2007/113226 | 10/2007 |
| WO | 2007/149395 | 12/2007 |
| WO | 2008/008539 | 1/2008 |
| WO | 2008/009487 | 1/2008 |
| WO | 2008/058037 | 5/2008 |
| WO | 2008/064157 | 5/2008 |
| WO | 2008/086014 | 7/2008 |
| WO | 2008/134553 | 11/2008 |
| WO | 2008/144253 | 11/2008 |
| WO | 2008/150015 | 12/2008 |
| WO | 2008/154642 | 12/2008 |
| WO | 2009/012283 | 1/2009 |
| WO | 2009/086277 | 7/2009 |
| WO | 2009/103778 | 8/2009 |
| WO | 2009/140128 | 11/2009 |
| WO | 2010/017047 | 2/2010 |
| WO | 2010/084425 | 7/2010 |
| WO | 2010/088000 | 8/2010 |
| WO | 2011/022439 | 2/2011 |
| WO | 2011/050245 | 4/2011 |
| WO | 2011/090738 | 7/2011 |
| WO | 2011/156655 | 12/2011 |
| WO | 2012/026765 | 3/2012 |
| WO | 2013/030802 | 3/2013 |

OTHER PUBLICATIONS

[No Author Listed] CAS STN Abstract 2008, RN 1007820-93-0.
Morphy, Selectively nonselective kinase inhibition: striking the right balance. J Med Chem. Feb. 25, 2010;53(4):1413-37.
Kim et al., Design and synthesis of imidazopyridine analogues as inhibitors of phosphoinositide 3-kinase signaling and angiogenesis. J Med Chem. Apr. 14, 2011;54(7):2455-66.

*Primary Examiner* — Heidi Reese
(74) *Attorney, Agent, or Firm* — Rona Nardone

(57) ABSTRACT

The present invention provides novel solid forms of pharmaceutically active agents and therapeutic uses thereof. The present invention further provides a combination of pharmacologically active agents and a pharmaceutical composition.

17 Claims, 15 Drawing Sheets

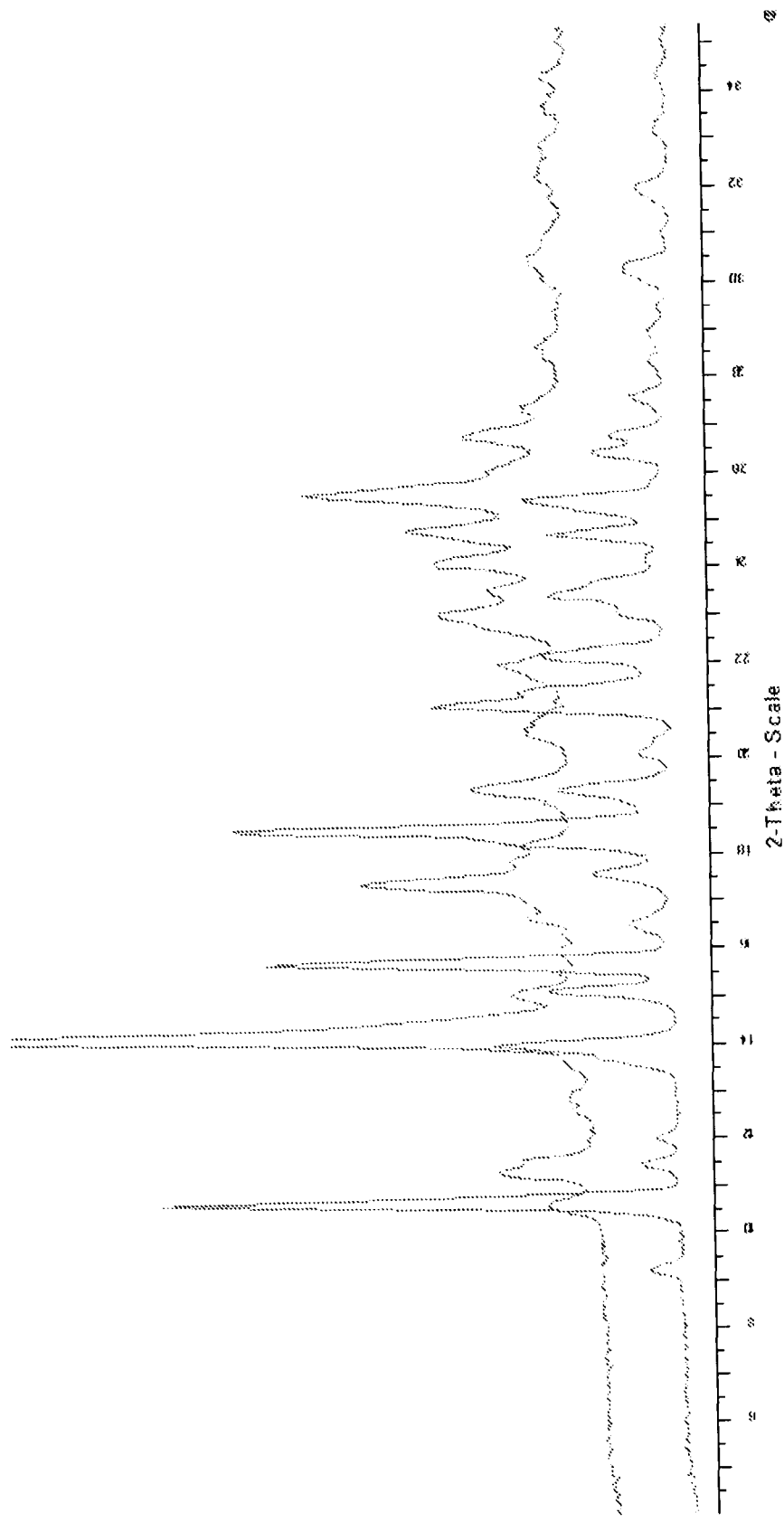
FIGURE 1 : XRPD of N-(5-(2-(2,6-cis- N-(5-(2-(2,6-cis-Dimethylpiperidin-1-yl)ethylcarbamoyl)-2-fluorophenyl)-7-(1-methyl-1H-pyrazol-5-yl)imidazo[1,2-a]pyridine-3-carboxamide Free Base (bottom) and Maleate (top)

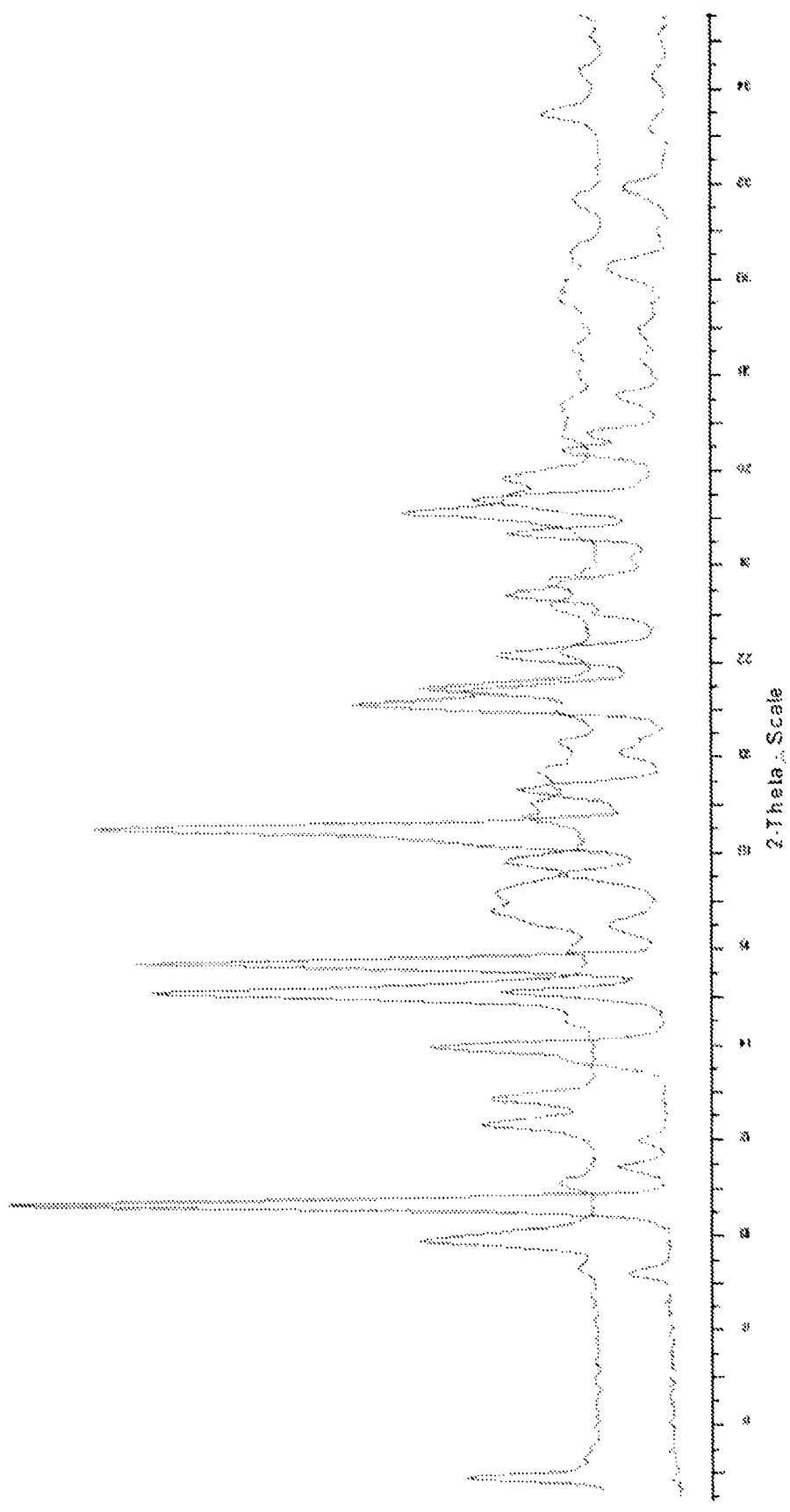
FIGURE 2: XRPD of N-(5-(2-(2,6-cis-Dimethylpiperidin-1-yl)ethylcarbamoyl)-2-fluorophenyl)-7-(1-methyl-1H-pyrazol-5-yl)imidazo[1,2-a]pyridine-3-carboxamide Free Base (bottom) and Saccharinate (top)

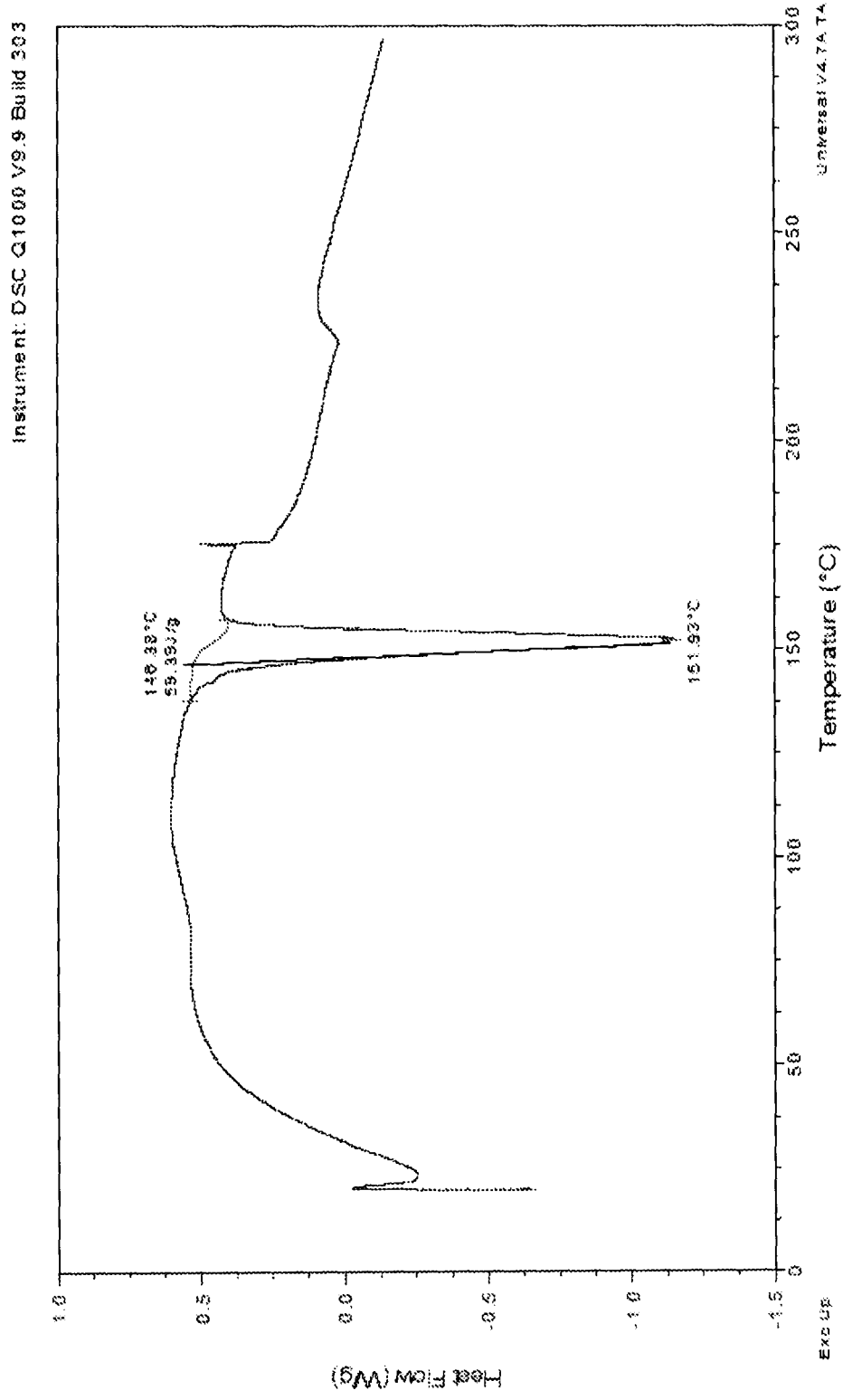
FIGURE 3: DSC of N-(5-(2-(2,6-cis- N-(5-(2-(2,6-cis-Dimethylpiperidin-1-yl)ethylcarbamoyl)-2-fluorophenyl)-7-(1-methyl-1H-pyrazol-5-yl)imidazo[1,2-a]pyridine-3-carboxamide Free Base (anhydrous). Plot shown with endothermic peaks pointing downwards.

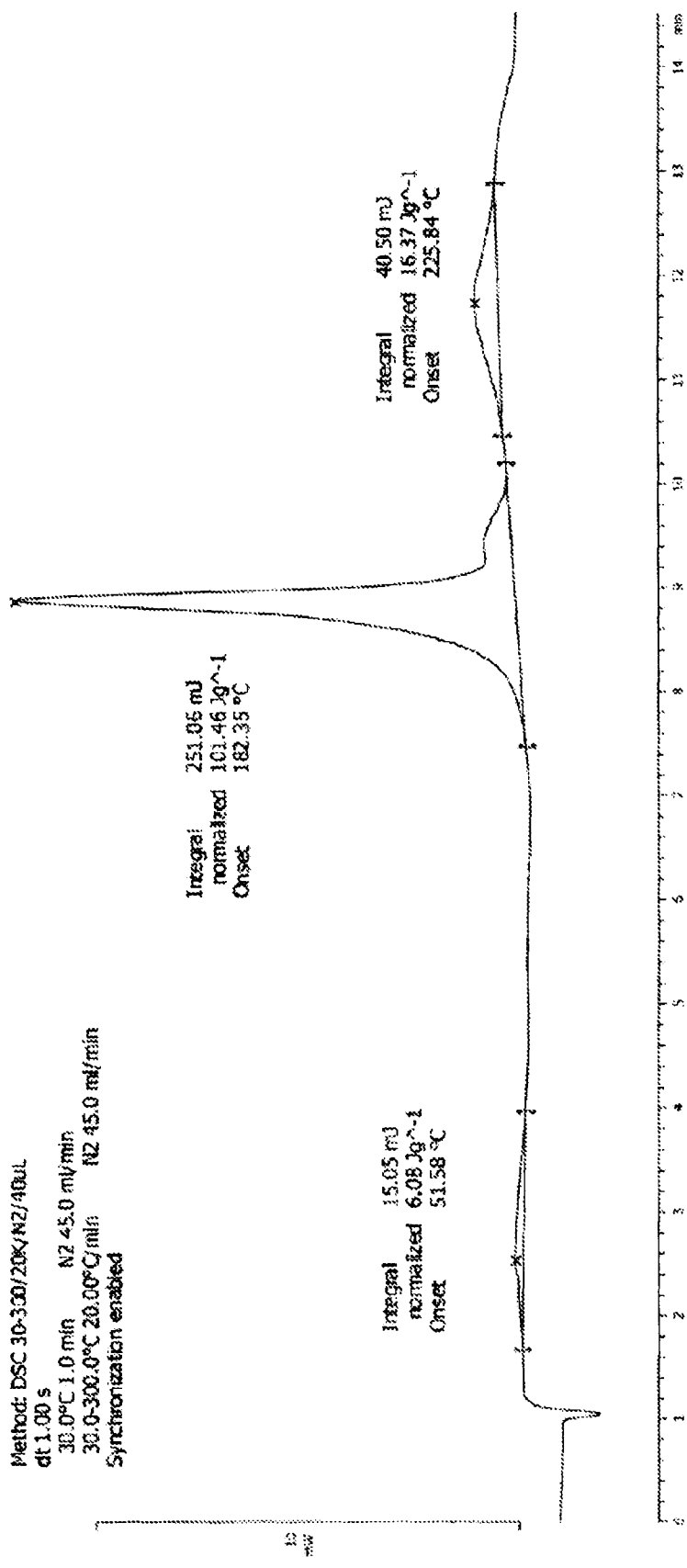
FIGURE 4: DSC of N-(5-(2-(2,6-cis- N-(5-(2-(2,6-cis-Dimethylpiperidin-1-yl)ethylcarbamoyl)-2-fluorophenyl)-7-(1-methyl-1H-pyrazol-5-yl)imidazo[1,2-a]pyridine-3-carboxamide Maleate

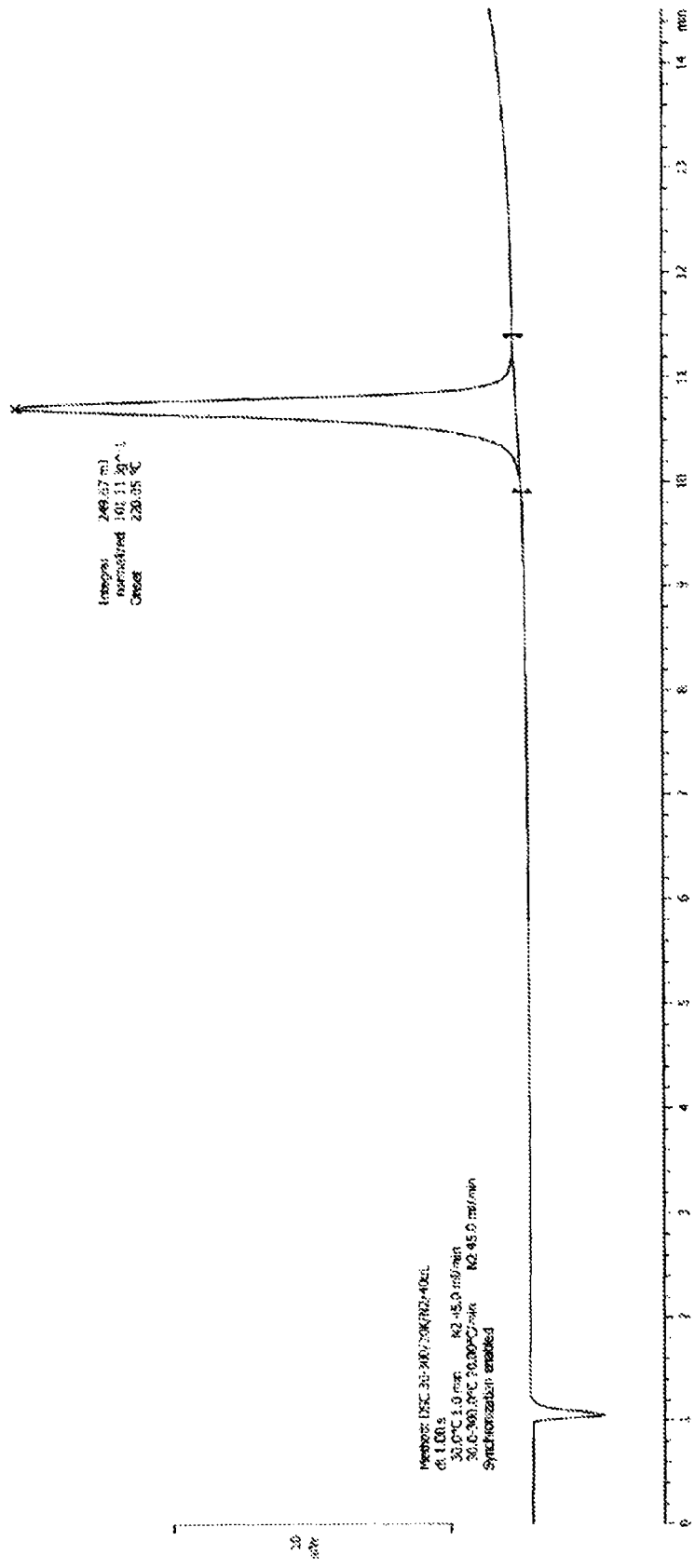
FIGURE 5: DSC of N-(5-(2-(2,6-cis- N-(5-(2-(2,6-cis-Dimethylpiperidin-1-yl)ethylcarbamoyl)-2-fluorophenyl)-7-(1-methyl-1H-pyrazol-5-yl)imidazo[1,2-a]pyridine-3-carboxamide Saccharinate

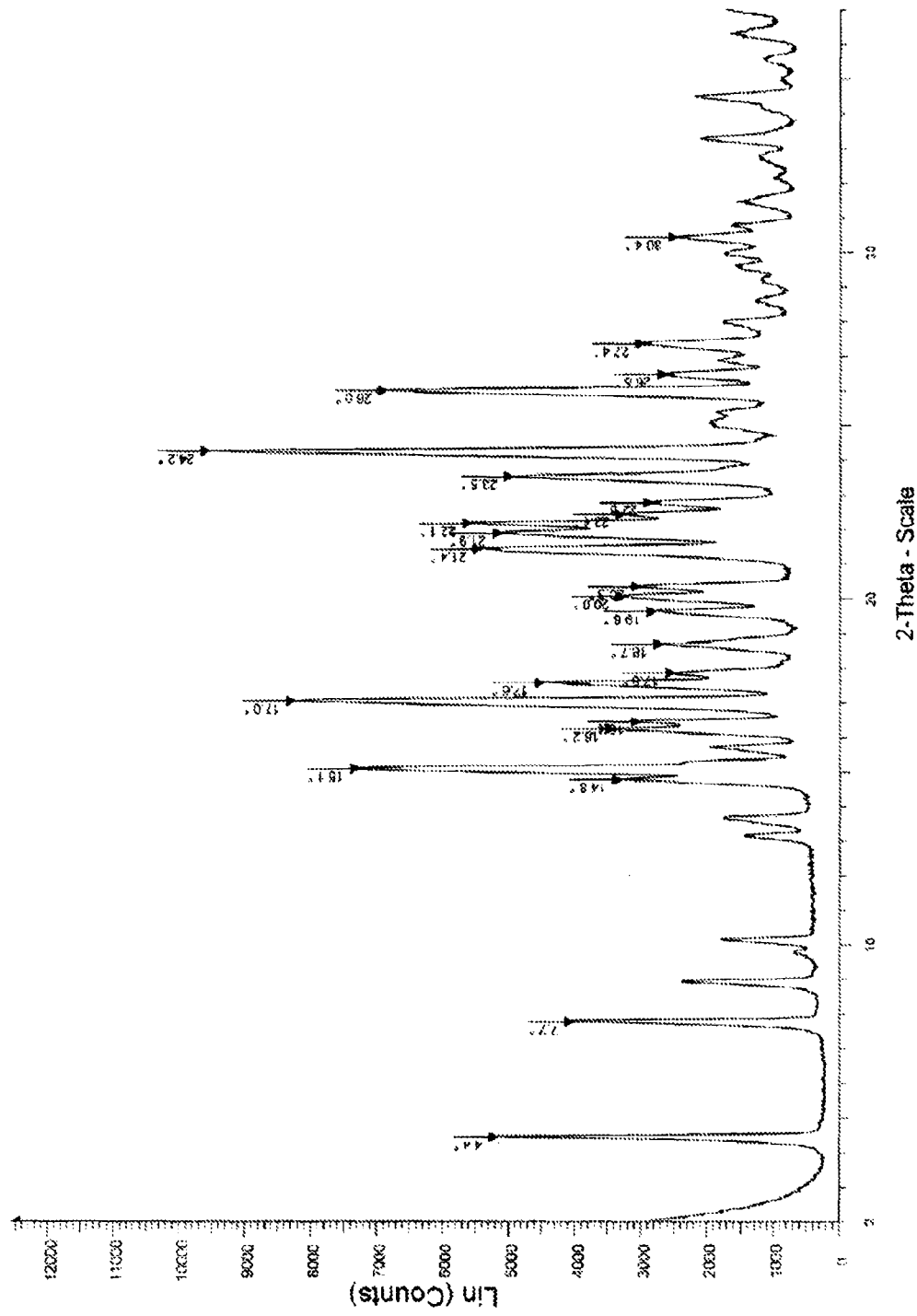
FIGURE 6a: XRPD of N-(5-(2-(2,2-dimethylpyrrolidin-1-yl)ethylcarbamoyl)-2-methylpyridin-3-yl)-6-(1-methyl-1H-pyrazol-4-yl)pyrazolo[1,5-a]pyridine-3-carboxamide L-Tartrate

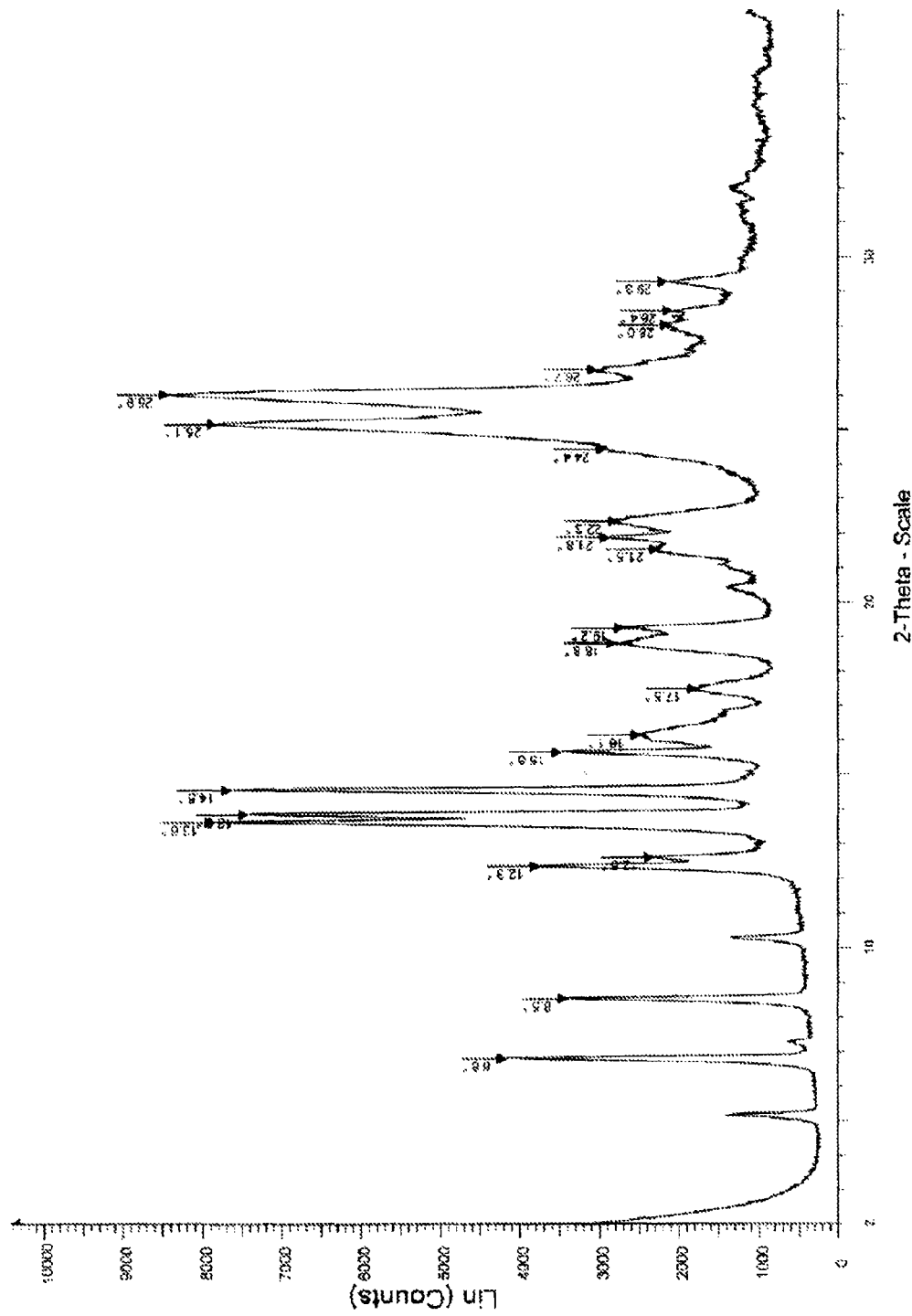
FIGURE 7a: XRPD of the Complex of N-(5-(2-(2,2-dimethylpyrrolidin-1-yl)ethylcarbamoyl)-2-methylpyridin-3-yl)-6-(1-methyl-1H-pyrazol-4-yl)pyrazolo[1,5-a]pyridine-3-carboxamide and Saccharin

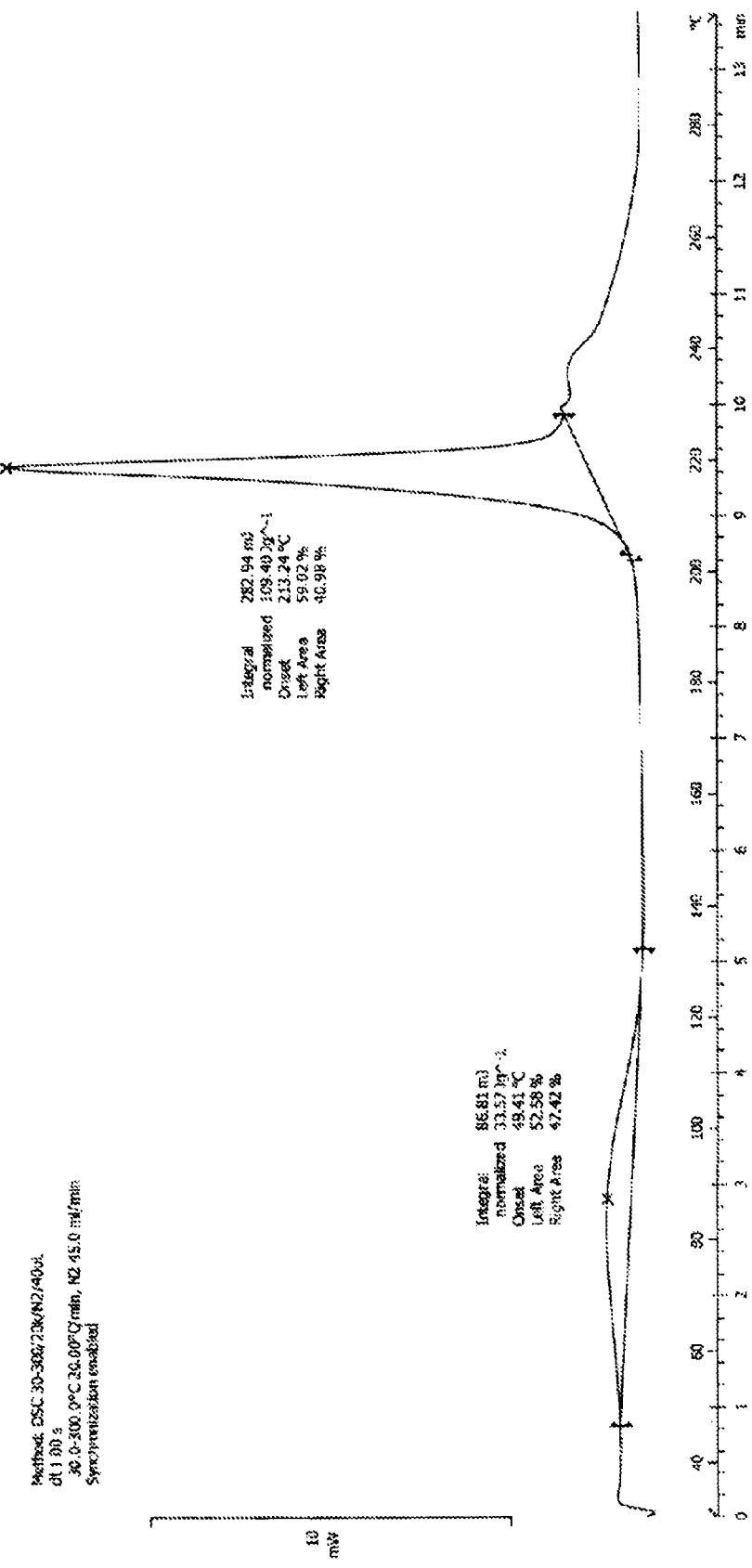
FIGURE 8: DSC of N-(5-(2-(2,2-dimethylpyrrolidin-1-yl)ethylcarbamoyl)-2-methylpyridin-3-yl)-6-(1-methyl-1H-pyrazol-4-yl)pyrazolo[1,5-a]pyridine-3-carboxamide L-Tartrate

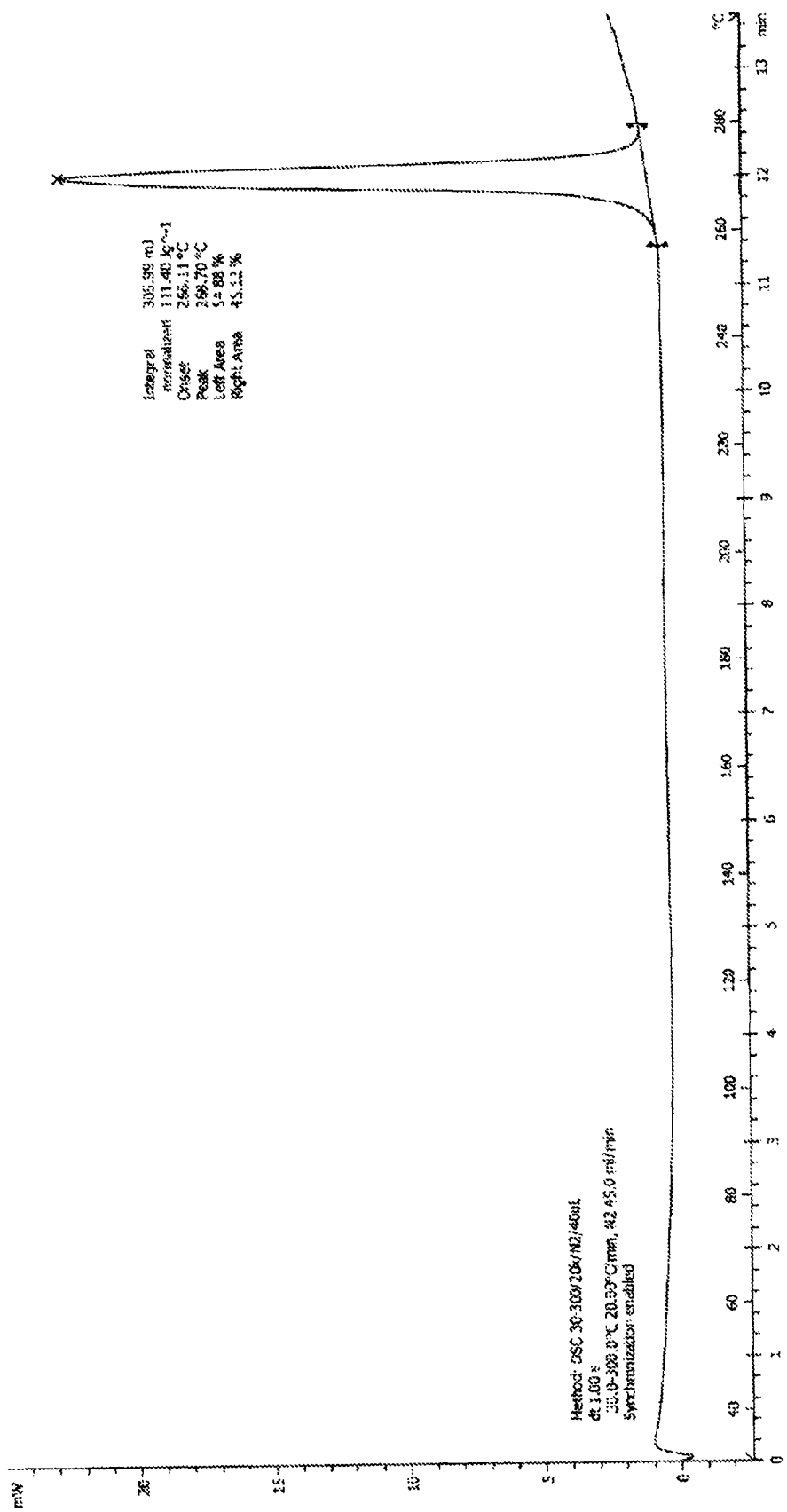
FIGURE 9: DSC of the Complex of N-(5-(2-(2,2-dimethylpyrrolidin-1-yl)ethylcarbamoyl)-2-methylpyridin-3-yl)-6-(1-methyl-1H-pyrazol-4-yl)pyrazolo[1,5-a]pyridine-3-carboxamide and Saccharin

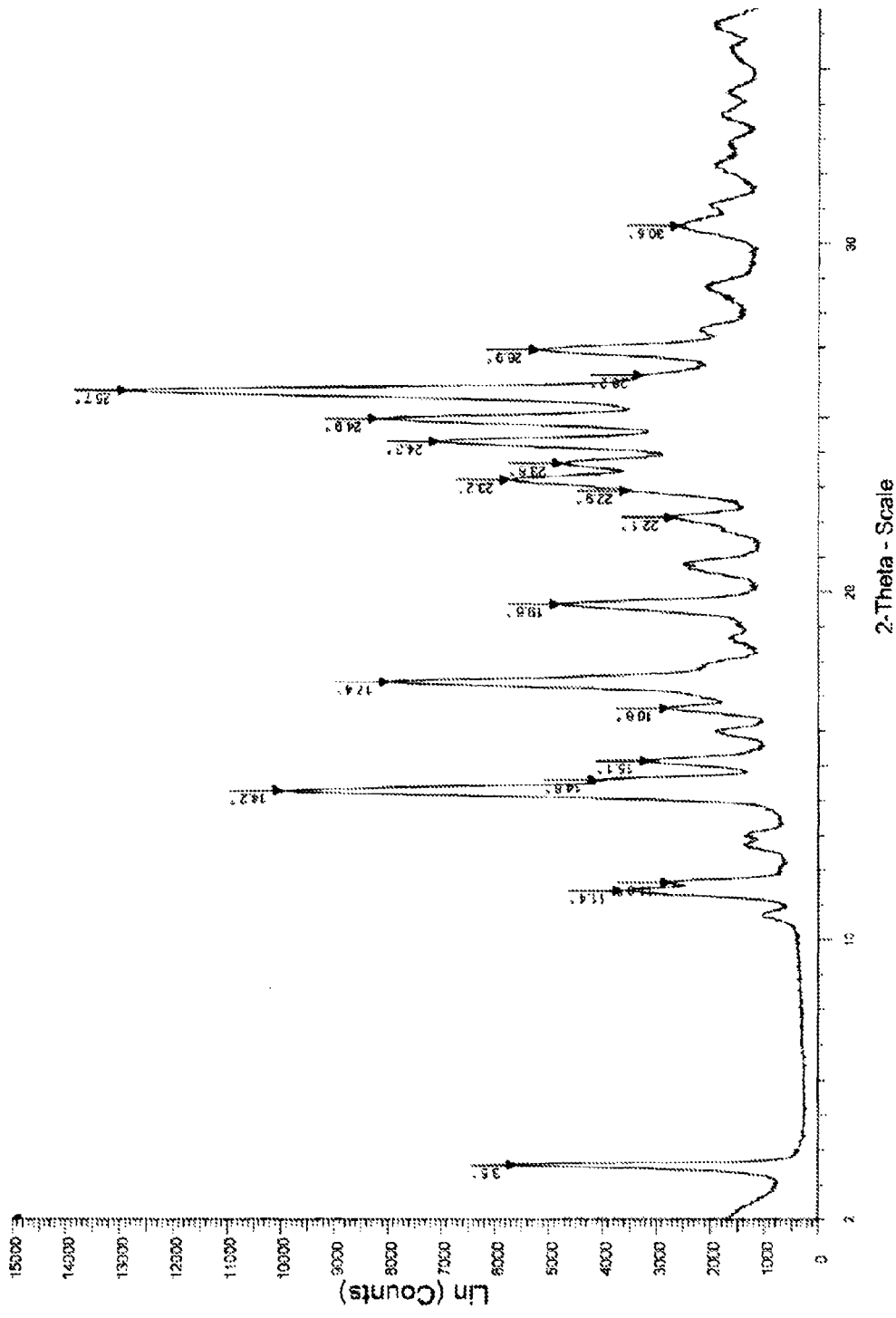
FIGURE 10a : XRPD of N-(5-(2-(2,6-cis- N-(5-(2-(2,6-cis-Dimethylpiperidin-1-yl)ethylcarbamoyl)-2-fluorophenyl)-7-(1-methyl-1H-pyrazol-5-yl)imidazo[1,2-a]pyridine-3-carboxamide Maleate

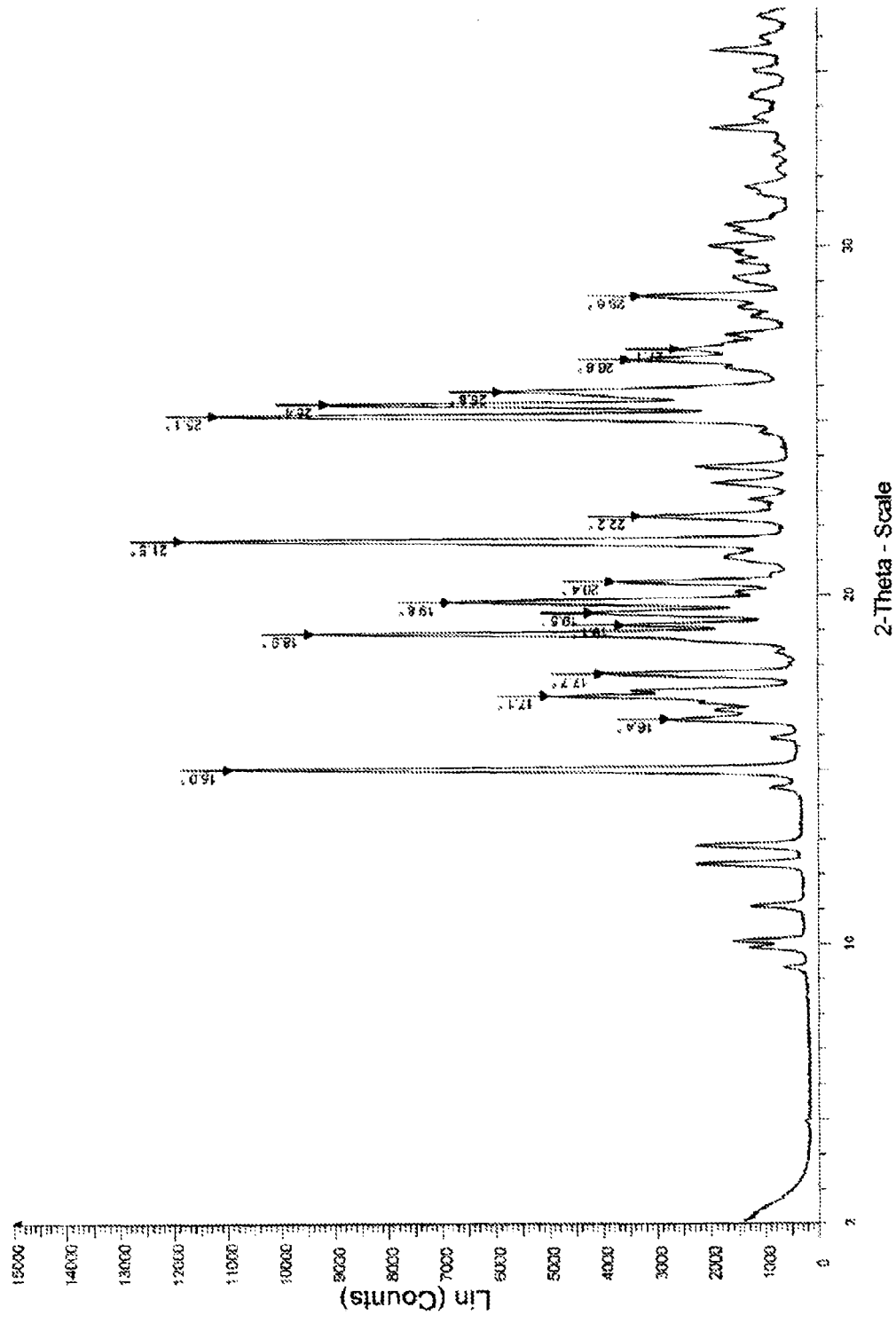
FIGURE 11a: XRPD of N-(5-(2-(2,6-cis-Dimethylpiperidin-1-yl)ethylcarbamoyl)-2-fluorophenyl)-7-(1-methyl-1H-pyrazol-5-yl)imidazo[1,2-a]pyridine-3-carboxamide Saccharinate

SALT FORMS OF BICYCLIC HETEROCYCLIC DERIVATIVES

FIELD OF THE INVENTION

The present invention relates to novel solid forms of pharmaceutically active agents, to pharmaceutical compositions comprising, and to the use of such solid forms.

BACKGROUND

The compounds N-(5-(2-(2,2-dimethylpyrrolidin-1-yl)ethylcarbamoyl)-2-methylpyridin-3-yl)-6-(1-methyl-1H-pyrazol-4-yl)pyrazolo[1,5-a]pyridine-3-carboxamide

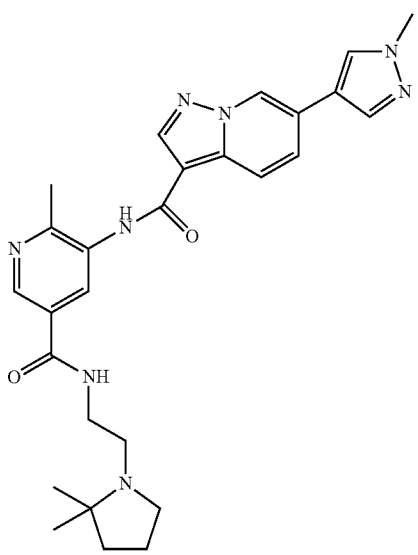 [SMILES: Cc1ncc(C(=O)NCCN2CCCC2(C)C)cc1NC(=O)c1cnn2cc(-c3cnn(C)c3)ccc12]

and
N-(5-(2-(2,6-cis-Dimethylpiperidin-1-yl)ethylcarbamoyl)-2-fluorophenyl)-7-(1-methyl-1H-pyrazol-5-yl)imidazo[1,2-a]pyridine-3-carboxamide

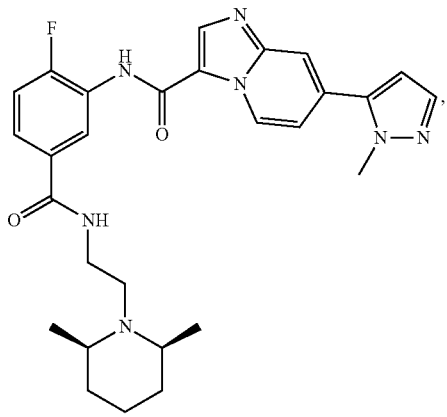 [SMILES: C[C@@H]1CCC[C@H](C)N1CCNC(=O)c1ccc(F)c(NC(=O)c2cnc3cc(-c4ccnn4C)ccn23)c1]

and methods for preparing the same, have been disclosed in co-pending international patent application PCT/IB2012/054501 (published as WO2013/030802).

N-(5-(2-(2,2-Dimethylpyrrolidin-1-yl)ethylcarbamoyl)-2-methylpyridin-3-yl)-6-(1-methyl-1H-pyrazol-4-yl)pyrazolo[1,5-a]pyridine-3-carboxamide and N-(5-(2-(2,6-cis-Dimethylpiperidin-1-yl)ethylcarbamoyl)-2-fluorophenyl)-7-(1-methyl-1H-pyrazol-5-yl)imidazo[1,2-a]pyridine-3-carboxamide are pharmaceutically active agents which act as PDGF receptor inhibitors and are useful in the treatment of respiratory, inflammatory and fibrotic diseases and conditions, for example pulmonary arterial hypertension (PAH).

SUMMARY OF THE INVENTION

Various embodiments of the invention are described herein.

In a first aspect, the invention provides a compound selected from:
N-(5-(2-(2,2-dimethylpyrrolidin-1-yl)ethylcarbamoyl)-2-methylpyridin-3-yl)-6-(1-methyl-1H-pyrazol-4-yl)pyrazolo[1,5-a]pyridine-3-carboxamide tartrate;
Complex of N-(5-(2-(2,2-dimethylpyrrolidin-1-yl)ethylcarbamoyl)-2-methylpyridin-3-yl)-6-(1-methyl-1H-pyrazol-4-yl)pyrazolo[1,5-a]pyridine-3-carboxamide and Saccharin;
N-(5-(2-(2,6-cis-Dimethylpiperidin-1-yl)ethylcarbamoyl)-2-fluorophenyl)-7-(1-methyl-1H-pyrazol-5-yl)imidazo[1,2-a]pyridine-3-carboxamide maleate; and
N-(5-(2-(2,6-cis-Dimethylpiperidin-1-yl)ethylcarbamoyl)-2-fluorophenyl)-7-(1-methyl-1H-pyrazol-5-yl)imidazo[1,2-a]pyridine-3-carboxamide saccharinate.

In a second aspect, the invention provides a pharmaceutical composition comprising a therapeutically effective amount of the compound according to the first aspect and one or more pharmaceutically acceptable carriers.

In a third aspect, the invention provides a method of treating a disorder or disease mediated by the PDGF receptor in a subject in need thereof, comprising administering to the subject in need thereof a therapeutically effective amount of the compound of the first aspect.

In a fourth aspect, the invention provides a combination comprising a therapeutically effective amount of the compound according to the first aspect and one or more therapeutically active agents.

BRIEF DESCRIPTION OF DRAWINGS

FIG. 1 illustrates the x-ray powder diffraction (XRPD) patterns of N-(5-(2-(2,6-cis-N-(5-(2-(2,6-cis-Dimethylpiperidin-1-yl)ethylcarbamoyl)-2-fluorophenyl)-7-(1-methyl-1H-pyrazol-5-yl)imidazo[1,2-a]pyridine-3-carboxamide Free Base and Maleate.

FIG. 2 illustrates the x-ray powder diffraction (XRPD) patterns of N-(5-(2-(2,6-cis-N-(5-(2-(2,6-cis-Dimethylpiperidin-1-yl)ethylcarbamoyl)-2-fluorophenyl)-7-(1-methyl-1H-pyrazol-5-yl)imidazo[1,2-a]pyridine-3-carboxamide Free Base and Saccharinate.

FIG. 3 illustrates the differential scanning calorimetry (DSC) of N-(5-(2-(2,6-cis-N-(5-(2-(2,6-cis-Dimethylpiperidin-1-yl)ethylcarbamoyl)-2-fluorophenyl)-7-(1-methyl-1H-pyrazol-5-yl)imidazo[1,2-a]pyridine-3-carboxamide Free Base (anhydrous).

FIG. 4 illustrates the differential scanning calorimetry (DSC) of N-(5-(2-(2,6-cis-N-(5-(2-(2,6-cis-Dimethylpiperidin-1-yl)ethylcarbamoyl)-2-fluorophenyl)-7-(1-methyl-1H-pyrazol-5-yl)imidazo[1,2-a]pyridine-3-carboxamide Maleate.

FIG. 5 illustrates the differential scanning calorimetry (DSC) of N-(5-(2-(2,6-cis-N-(5-(2-(2,6-cis-Dimethylpiperidin-1-yl)ethylcarbamoyl)-2-fluorophenyl)-7-(1-methyl-1H-pyrazol-5-yl)imidazo[1,2-a]pyridine-3-carboxamide Saccharinate.

FIG. 8 illustrates the differential scanning calorimetry (DSC) of N-(5-(2-(2,2-dimethylpyrrolidin-1-yl)ethylcarbamoyl)-2-methylpyridin-3-yl)-6-(1-methyl-1H-pyrazol-4-yl)pyrazolo[1,5-a]pyridine-3-carboxamide L-Tartrate.

FIG. 9 illustrates the differential scanning calorimetry (DSC) of the Complex of N-(5-(2-(2,2-dimethylpyrrolidin-1-yl)ethylcarbamoyl)-2-methylpyridin-3-yl)-6-(1-methyl-1H-pyrazol-4-yl)pyrazolo[1,5-a]pyridine-3-carboxamide and Saccharin.

DETAILED DESCRIPTION

Embodiment 1: A compound selected from
N-(5-(2-(2,2-dimethylpyrrolidin-1-yl)ethylcarbamoyl)-2-methylpyridin-3-yl)-6-(1-methyl-1H-pyrazol-4-yl)pyrazolo[1,5-a]pyridine-3-carboxamide tartrate;
Complex of N-(5-(2-(2,2-dimethylpyrrolidin-1-yl)ethylcarbamoyl)-2-methylpyridin-3-yl)-6-(1-methyl-1H-pyrazol-4-yl)pyrazolo[1,5-a]pyridine-3-carboxamide and Saccharin;
N-(5-(2-(2,6-cis-Dimethylpiperidin-1-yl)ethylcarbamoyl)-2-fluorophenyl)-7-(1-methyl-1H-pyrazol-5-yl)imidazo[1,2-a]pyridine-3-carboxamide maleate; and
N-(5-(2-(2,6-cis-Dimethylpiperidin-1-yl)ethylcarbamoyl)-2-fluorophenyl)-7-(1-methyl-1H-pyrazol-5-yl)imidazo[1,2-a]pyridine-3-carboxamide saccharinate.

Embodiment 2: A compound selected from
N-(5-(2-(2,2-dimethylpyrrolidin-1-yl)ethylcarbamoyl)-2-methylpyridin-3-yl)-6-(1-methyl-1H-pyrazol-4-yl)pyrazolo[1,5-a]pyridine-3-carboxamide tartrate;
N-(5-(2-(2,2-dimethylpyrrolidin-1-yl)ethylcarbamoyl)-2-methylpyridin-3-yl)-6-(1-methyl-1H-pyrazol-4-yl)pyrazolo[1,5-a]pyridine-3-carboxamide L-tartrate
Complex of N-(5-(2-(2,2-dimethylpyrrolidin-1-yl)ethylcarbamoyl)-2-methylpyridin-3-yl)-6-(1-methyl-1H-pyrazol-4-yl)pyrazolo[1,5-a]pyridine-3-carboxamide and Saccharin; and
N-(5-(2-(2,2-dimethylpyrrolidin-1-yl)ethylcarbamoyl)-2-methylpyridin-3-yl)-6-(1-methyl-1H-pyrazol-4-yl)pyrazolo[1,5-a]pyridine-3-carboxamide saccharinate.

Embodiment 3: A compound selected from
N-(5-(2-(2,6-cis-Dimethylpiperidin-1-yl)ethylcarbamoyl)-2-fluorophenyl)-7-(1-methyl-1H-pyrazol-5-yl)imidazo[1,2-a]pyridine-3-carboxamide maleate; and
N-(5-(2-(2,6-cis-Dimethylpiperidin-1-yl)ethylcarbamoyl)-2-fluorophenyl)-7-(1-methyl-1H-pyrazol-5-yl)imidazo[1,2-a]pyridine-3-carboxamide saccharinate.

Embodiment 4: A crystalline form of N-(5-(2-(2,2-dimethylpyrrolidin-1-yl)ethylcarbamoyl)-2-methylpyridin-3-yl)-6-(1-methyl-1H-pyrazol-4-yl)pyrazolo[1,5-a]pyridine-3-carboxamide L-tartrate.

Embodiment 4.1: The crystalline form according to Embodiment 4, characterized by a X-ray powder diffraction pattern comprising four or more 2Θ values selected from the group consisting of 15.1±0.2°, 17.0±0.2°, 21.4±0.2°, 22.1±0.2°, 24.2±0.2° and 26.0±0.2° at a temperature of about 25° C.

Embodiment 4.2: The crystalline form according to Embodiment 4, characterized by a X-ray powder diffraction pattern comprising five or more 2Θ values 2Θ values selected from the group consisting of 4.4±0.2°, 7.7±0.2°, 14.8±0.2°, 15.1±0.2°, 16.2±0.2°, 16.4±0.2°, 17.0±0.2°, 17.6±0.2°, 17.8±0.2°, 18.7±0.2°, 19.6±0.2°, 20.0±0.2°, 20.3±0.2°, 21.4±0.2°, 21.9±0.2°, 22.1±0.2°, 22.4±0.2°, 22.6±0.2°, 23.5±0.2°, 24.2±0.2°, 26.0±0.2°, 26.5±0.2° and 27.4±0.2° at a temperature of about 25° C.

Figure 6B:
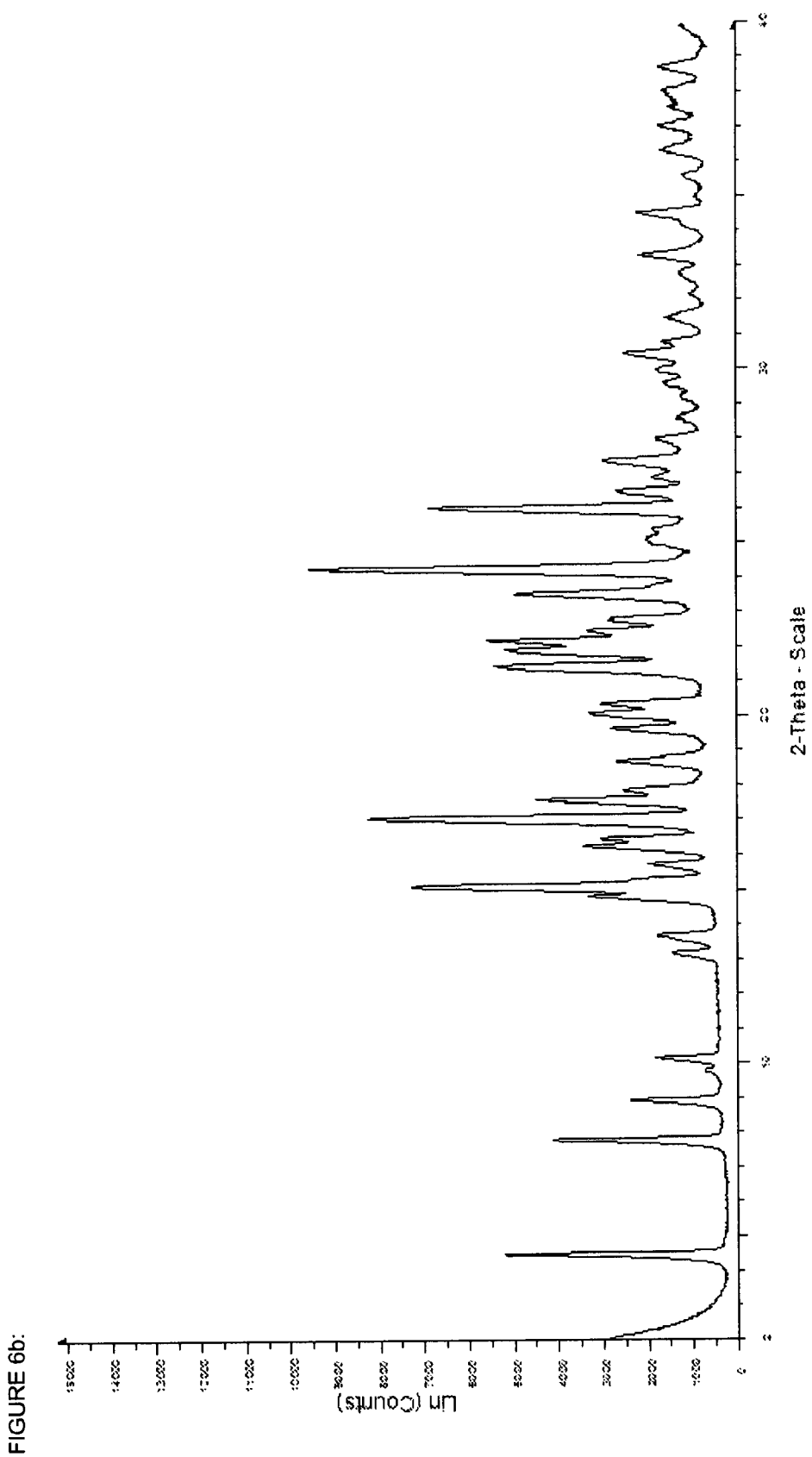
FIG. 6 illustrates the x-ray powder diffraction (XRPD) pattern of N-(5-(2-(2,2-dimethylpyrrolidin-1-yl)ethylcarbamoyl)-2-methylpyridin-3-yl)-6-(1-methyl-1H-pyrazol-4-yl)pyrazolo[1,5-a]pyridine-3-carboxamide L-Tartrate. The XRPD pattern is shown with and without peak markings.

Embodiment 4.3: The crystalline form according to Embodiment 4, characterized by a X-ray powder diffraction spectrum substantially the same as the X-ray powder diffraction spectrum shown in FIG. 6

Embodiment 4.4: The crystalline form according to Embodiment 4, characterized by a differential scanning calorimetry (DSC) thermogram substantially the same as that shown in FIG. 8.

Embodiment 4.5: The crystalline form according to Embodiment 4, characterized by a differential scanning calorimetry (DSC) thermogram comprising an endotherm onset at around 213° C.

Embodiment 5: A crystalline form of N-(5-(2-(2,2-dimethylpyrrolidin-1-yl)ethylcarbamoyl)-2-methylpyridin-3-yl)-6-(1-methyl-1H-pyrazol-4-yl)pyrazolo[1,5-a]pyridine-3-carboxamide saccharinate.

Embodiment 5.1: The crystalline form according to Embodiment 5, characterized by a X-ray powder diffraction pattern comprising four or more 2Θ values selected from the group consisting of 13.4±0.2°, 13.7±0.2°, 14.4±0.2°, 15.5±0.2°, 25.1±0.2° and 26.0±0.2° at a temperature of about 25° C.

Embodiment 5.2: The crystalline form according to Embodiment 5, characterized by a X-ray powder diffraction pattern comprising five or more 2Θ values selected from the group consisting of 6.7±0.2°, 8.4±0.2°, 12.3±0.2°, 13.4±0.2°, 13.7±0.2°, 14.4±0.2°, 15.5±0.2°, 21.2±0.2°, 21.7±0.2°, 25.1±0.2°, 25.6±0.2° and 26.0±0.2° at a temperature of about 25° C.

Figure 7B:
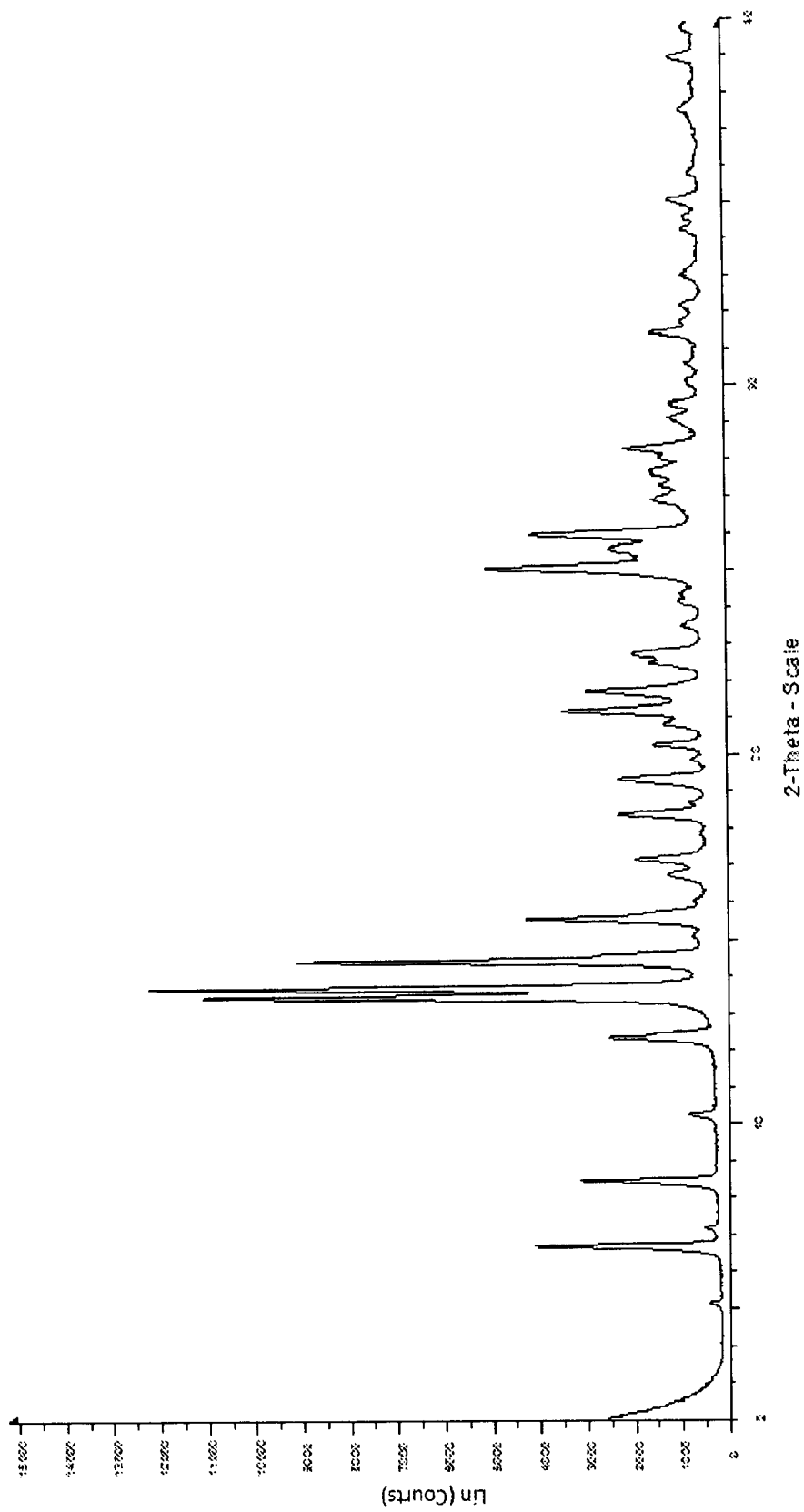
FIG. 7 illustrates the x-ray powder diffraction (XRPD) pattern of the Complex of N-(5-(2-(2,2-dimethylpyrrolidin-1-yl)ethylcarbamoyl)-2-methylpyridin-3-yl)-6-(1-methyl-1H-pyrazol-4-yl)pyrazolo[1,5-a]pyridine-3-carboxamide and Saccharin. The XRPD pattern is shown with and without peak markings.

Embodiment 5.3: The crystalline form according to Embodiment 5, characterized by a X-ray powder diffraction spectrum substantially the same as the X-ray powder diffraction spectrum shown in FIG. 7

Embodiment 5.4: The crystalline form according to Embodiment 5, characterized by a differential scanning calorimetry (DSC) thermogram substantially the same as that shown in FIG. 9.

Embodiment 5.5: The crystalline form according to Embodiment 5, characterized by a differential scanning calorimetry (DSC) thermogram comprising an endotherm onset at around 266° C.

Embodiment 6: A crystalline form of N-(5-(2-(2,6-cis-Dimethylpiperidin-1-yl)ethylcarbamoyl)-2-fluorophenyl)-7-(1-methyl-1H-pyrazol-5-yl)imidazo[1,2-a]pyridine-3-carboxamide maleate.

Embodiment 6.1: The crystalline form according to Embodiment 6, characterized by a X-ray powder diffraction pattern comprising four or more 2Θ values selected from the group consisting 14.2±0.2°, 17.4±0.2°, 24.3±0.2°, 24.9±0.2° and 25.7±0.2° at a temperature of about 25° C.

Embodiment 6.2: The crystalline form according to Embodiment 6, characterized by a X-ray powder diffraction pattern comprising five or more 2Θ values selected from the group consisting of 3.5±0.2°, 11.4±0.2°, 11.6±0.2°, 14.2±0.2°, 14.6±0.2°, 15.1±0.2°, 16.6±0.2°, 17.4±0.2°, 19.6±0.2°, 19.6±0.2°, 22.1±0.2°, 22.9±0.2°, 23.2±0.2°, 23.6±0.2°, 24.3±0.2°, 24.9±0.2°, 25.7±0.2°, 26.2±0.2°, 26.9±0.2° and 30.5±0.2° at a temperature of about 25° C.

Figure 10B:
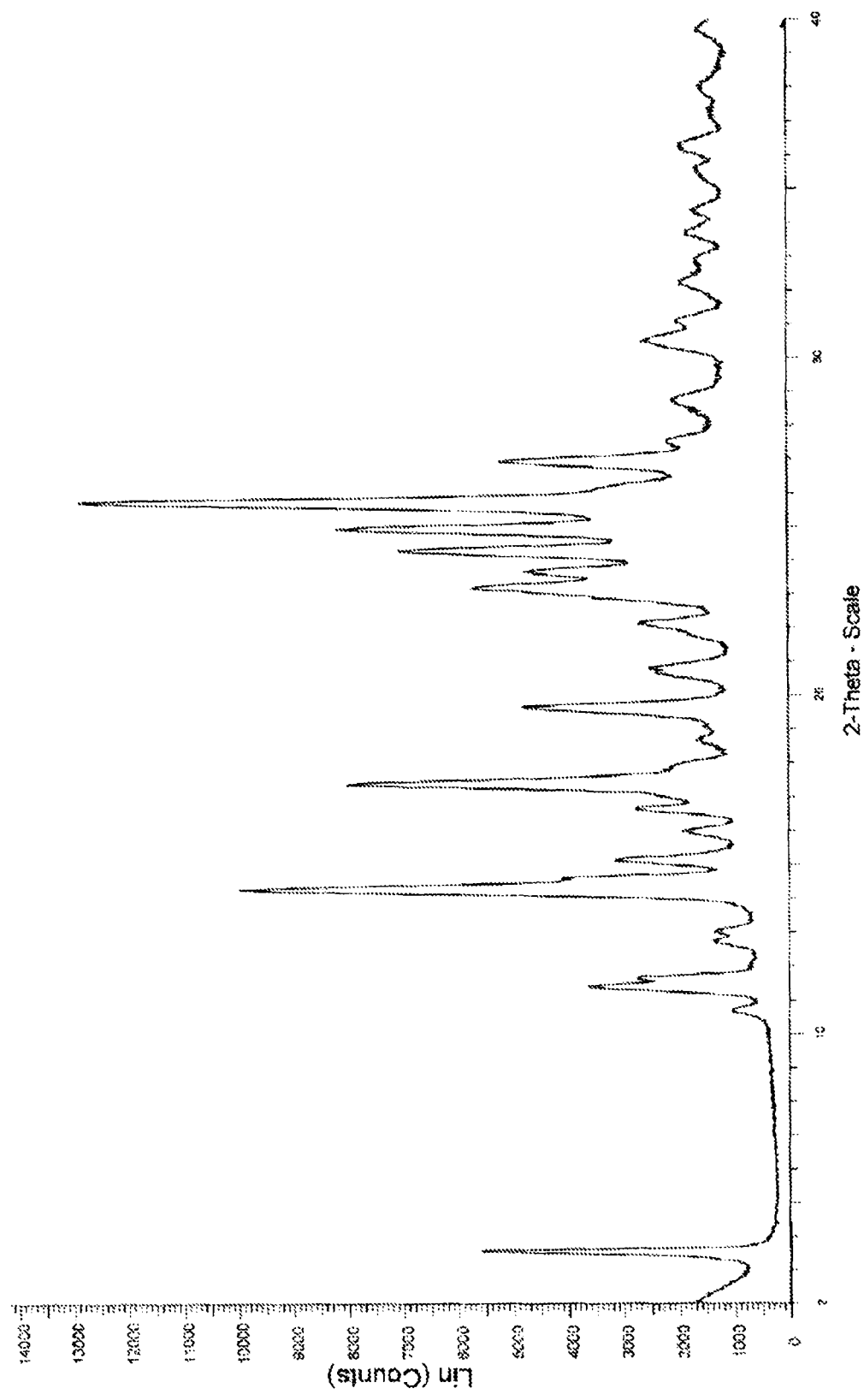
FIG. 10 illustrates the x-ray powder diffraction (XRPD) pattern of N-(5-(2-(2,6-cis-N-(5-(2-(2,6-cis-Dimethylpiperidin-1-yl)ethylcarbamoyl)-2-fluorophenyl)-7-(1-methyl-1H-pyrazol-5-yl)imidazo[1,2-a]pyridine-3-carboxamide Maleate. The XRPD pattern is shown with and without peak markings.

Embodiment 6.3: The crystalline form according to Embodiment 6, characterized by a X-ray powder diffraction spectrum substantially the same as the X-ray powder diffraction spectrum shown in FIG. 10

Embodiment 6.4: The crystalline form according to Embodiment 6, characterized by a differential scanning calorimetry (DSC) thermogram substantially the same as that shown in FIG. 4.

Embodiment 6.5: The crystalline form according to Embodiment 6, characterized by a differential scanning calorimetry (DSC) thermogram comprising an endotherm onset at around 182° C.

Embodiment 7: A crystalline form of N-(5-(2-(2,6-cis-Dimethylpiperidin-1-yl)ethylcarbamoyl)-2-fluorophenyl)-7-(1-methyl-1H-pyrazol-5-yl)imidazo[1,2-a]pyridine-3-carboxamide saccharinate.

Embodiment 7.1: The crystalline form according, to Embodiment 7, characterized by a X-ray powder diffraction pattern comprising four or more 2Θ values selected from the group consisting of [group of peaks 15.0±0.2°, 18.9±0.2°, 19.8±0.2°, 21.5±0.2°, 25.1±0.2° and 25.4±0.2° at a temperature of about 25° C.

Embodiment 7.2: The crystalline form according to Embodiment 7, characterized by a X-ray powder diffraction pattern comprising five or more 2Θ values selected from the group consisting of 15.0±0.2°, 16.4±0.2°, 17.1±0.2°, 17.7±0.2°, 18.9±0.2°, 19.1±0.2°, 19.5±0.2°, 19.8±0.2°, 20.4±0.2°, 21.5±0.2°, 22.2±0.2°, 25.1±0.2°, 25.4±0.2°, 25.8±0.2°, 26.8±0.2°, 27.1±0.2° and 28.6±0.2° at a temperature of about 25° C.

Figure 11B:
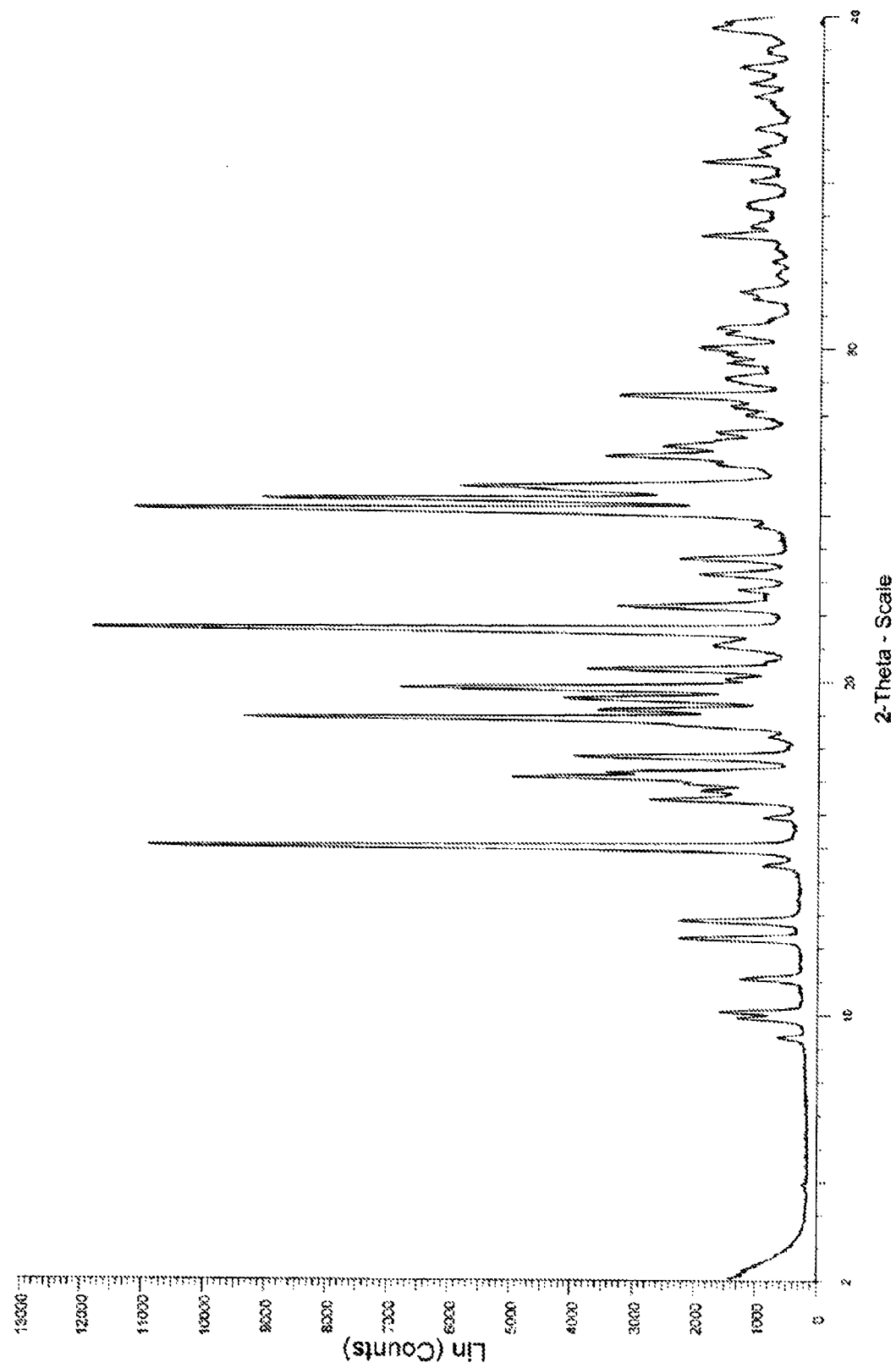
FIG. 11 illustrates the x-ray powder diffraction (XRPD) pattern of N-(5-(2-(2,6-cis-N-(5-(2-(2,6-cis-Dimethylpiperidin-1-yl)ethylcarbamoyl)-2-fluorophenyl)-7-(1-methyl-1H-pyrazol-5-yl)imidazo[1,2-a]pyridine-3-carboxamide Saccharinate. The XRPD pattern is shown with and without peak markings.

Embodiment 7.3: The crystalline form according to Embodiment 7, characterized by a X-ray powder diffraction spectrum substantially the same as the X-ray powder diffraction spectrum shown in FIG. 11

Embodiment 7.4: The crystalline form according to Embodiment 7, characterized by a differential scanning calorimetry (DSC) thermogram substantially the same as that shown in FIG. 5.

Embodiment 7.5: The crystalline form according to Embodiment 7, characterized by a differential scanning calorimetry (DSC) thermogram comprising an endotherm onset at around 220° C.

Embodiment 8: A pharmaceutical composition comprising a therapeutically effective amount of a compound according to any one of Embodiments 1 to 7.5 and one or more pharmaceutically acceptable carriers.

Embodiment 8.1: A pharmaceutical composition comprising a therapeutically effective amount of a compound according to any two or more of Embodiments 1 to 7.5 and one or more pharmaceutically acceptable carriers.

Embodiment 9: A pharmaceutical composition according to Embodiment 8, wherein the composition further comprises one or more additional therapeutically active agents.

Embodiment 10: A method of treating a disorder or disease mediated by the PDGF receptor in a subject in need thereof, comprising administering to the subject in need thereof a therapeutically effective amount of a compound according to any one of Embodiments 1 to 7.5.

Embodiment 11: The method according to Embodiment 10, wherein the disease or disorder is selected from respiratory, inflammatory and fibrotic diseases and conditions, for example pulmonary arterial hypertension.

Embodiment 12: A compound according to any one of Embodiments 1 to 7.5, for use as a medicament.

Embodiment 13: A compound according to any one of Embodiments 1 to 7.5, for use in the treatment of a disorder or disease mediated by the PDGF receptor.

Embodiment 14: A compound according to Embodiment 13, wherein the disease or disorder is selected from respiratory, inflammatory and fibrotic diseases and conditions, for example pulmonary arterial hypertension.

Embodiment 15: Use of a compound according to any one of Embodiments 1 to 7.5 in the manufacture of a medicament for the treatment of a disorder or disease mediated by the PDGF receptor.

Embodiment 16: The use according to Embodiment 15, wherein the disease or disorder is selected from respiratory, inflammatory and fibrotic diseases and conditions, for example pulmonary arterial hypertension.

Embodiment 17: A combination comprising a therapeutically effective amount of a compound according to any one of Embodiments 1 to 7.5 and one or more therapeutically active agents.

As used herein, the term 'solid form' or 'complex' refers to both 'salts and 'co-crystals' formed by the interaction of N-(5-(2-(2,2-Dimethylpyrrolidin-1-yl)ethylcarbamoyl)-2-methylpyridin-3-yl)-6-(1-methyl-1H-pyrazol-4-yl)pyrazolo[1,5-a]pyridine-3-carboxamide or N-(5-(2-(2,6-cis-Dimethylpiperidin-1-yl)ethylcarbamoyl)-2-fluorophenyl)-7-(1-methyl-1 H-pyrazol-5-yl)imidazo[1,2-a]pyridine-3-carboxamide with a suitable counter-ion or co-crystal former.

As used herein, the terms "salt" or "salts" refers to an acid addition salt of N-(5-(2-(2,2-Dimethylpyrrolidin-1-yl)ethylcarbamoyl)-2-methylpyridin-3-yl)-6-(1-methyl-1 H-pyrazol-4-yl)pyrazolo[1,5-a]pyridine-3-carboxamide or N-(5-(2-(2,6-cis-Dimethylpiperidin-1-yl)ethylcarbamoyl)-2-fluorophenyl)-7-(1-methyl-1 H-pyrazol-5-yl)imidazo[1,2-a]pyridine-3-carboxamide.

The compounds N-(5-(2-(2,2-Dimethylpyrrolidin-1-yl)ethylcarbamoyl)-2-methylpyridin-3-yl)-6-(1-methyl-1H-pyrazol-4-yl)pyrazolo[1,5-a]pyridine-3-carboxamide and N-(5-(2-(2,6-cis-Dimethylpiperidin-1-yl)ethylcarbamoyl)-2-fluorophenyl)-7-(1-methyl-1 H-pyrazol-5-yl)imidazo[1,2-a]pyridine-3-carboxamide contain groups capable of acting as donors and/or acceptors for hydrogen bonds and may be capable of forming co-crystals with suitable co-crystal formers. These co-crystals may be prepared from the free base by known co-crystal forming procedures. Such procedures include grinding, heating, co-subliming, co-melting, or contacting in solution said the free base with the co-crystal former under crystallization conditions and isolating co-crystals thereby formed.

As used herein, the term 'Complex of N-(5-(2-(2,2-dimethylpyrrolidin-1-yl)ethylcarbamoyl)-2-methylpyridin-3-yl)-6-(1-methyl-1 H-pyrazol-4-yl)pyrazolo[1,5-a]pyridine-3-carboxamide and Saccharin' refers to a salt or co-crystal form prepared from the free base of N-(5-(2-(2,2-dimethylpyrrolidin-1-yl)ethylcarbamoyl)-2-methylpyridin-3-yl)-6-(1-methyl-1H-pyrazol-4-yl)pyrazolo[1,5-a]pyridine-3-carboxamide and Saccharin.

In one aspect, the Complex of N-(5-(2-(2,2-dimethylpyrrolidin-1-yl)ethylcarbamoyl)-2-methylpyridin-3-yl)-6-(1-methyl-1H-pyrazol-4-yl)pyrazolo[1,5-a]pyridine-3-carboxamide and Saccharin is a salt form (N-(5-(2-(2,2-dimethylpyrrolidin-1-yl)ethylcarbamoyl)-2-methylpyridin-3-yl)-6-(1-methyl-1H-pyrazol-4-yl)pyrazolo[1,5-a]pyridine-3-carboxamide Saccharinate).

In a further aspect, the Complex of N-(5-(2-(2,2-dimethylpyrrolidin-1-yl)ethylcarbamoyl)-2-methylpyridin-3-yl)-6-(1-methyl-1H-pyrazol-4-yl)pyrazolo[1,5-a]pyridine-3-carboxamide and Saccharin is a co-crystal of N-(5-(2-(2,2-dimethylpyrrolidin-1-yl)ethylcarbamoyl)-2-methylpyridin-3-yl)-6-(1-methyl-1H-pyrazol-4-yl)pyrazolo[1,5-a]pyridine-3-carboxamide and Saccharin.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) mediated by PDGFR or (ii) associated with PDGFR activity, or (iii) characterized by activity (normal or abnormal) of PDGFR; or (2) reducing or inhibiting the activity of PDGFR. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of PDGFR.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

The compounds of the present invention can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including hydrates and solvates thereof, may inherently or by design form polymorphs.

In another aspect, the present invention provides a pharmaceutical composition comprising a compound of the present invention, or a pharmaceutically acceptable salt thereof, and a pharmaceutically acceptable carrier. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers, etc.

Typically, the pharmaceutical compositions are tablets or gelatin capsules comprising the active ingredient together with a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

Where the inhalable form of the active ingredient is an aerosol composition, the inhalation device may be an aerosol vial provided with a valve adapted to deliver a metered dose, such as 10 to 100 µl, e.g. 25 to 50 µ of the composition, i.e. a device known as a metered dose inhaler. Suitable such aerosol vials and procedures for containing within them aerosol compositions under pressure are well known to those skilled in the art of inhalation therapy. For example, an aerosol composition may be administered from a coated can, for example as described in EP-A-0642992. Where the inhalable form of the active ingredient is a nebulizable aqueous, organic or aqueous/organic dispersion, the inhalation device may be a known nebulizer, for example a conventional pneumatic nebulizer such as an airjet nebulizer, or an ultrasonic nebulizer, which may contain, for example, from 1 to 50 ml, commonly 1 to 10 ml, of the dispersion; or a hand-held nebulizer, sometimes referred to as a soft mist or soft spray inhaler, for example an electronically controlled device such as an AERx (Aradigm, US) or Aerodose (Aerogen), or a mechanical device such as a RESPIMAT (Boehringer Ingelheim) nebulizer which allows much smaller nebulized volumes, e.g. 10 to 100 µ than conventional nebulizers. Where the inhalable form of the active ingredient is the finely divided particulate form, the inhalation device may be, for example, a dry powder inhalation device adapted to deliver dry powder from a capsule or blister containing a dry powder comprising a dosage unit of (A) and/or (B) or a multidose dry powder inhalation (MDPI) device adapted to deliver, for example, 3-25 mg of dry powder comprising a dosage unit of (A) and/or (B) per actuation. The dry powder composition preferably contains a diluent or carrier, such as lactose, and a compound that helps to protect against product performance deterioration due to moisture e.g. magnesium stearate. Suitable such dry powder inhalation devices include devices disclosed in U.S. Pat. No. 3,991,761 (including the AEROLIZERTM device), WO 05/113042, WO 97/20589 (including the CERTIHALER™ device), WO 97/30743 (including the TWISTHALER™ device) and WO 05/37353 (including the GYROHALER™ device).

The invention also includes (A) an agent of the invention in inhalable form; (B) an inhalable medicament comprising such a compound in inhalable form together with a pharmaceutically acceptable carrier in inhalable form; (C) a pharmaceutical product comprising such a compound in inhalable form in association with an inhalation device; and (D) an inhalation device containing such a compound in inhalable form.

Dosages of agents of the invention employed in practising the present invention will of course vary depending, for example, on the particular condition to be treated, the effect desired and the mode of administration. In general, suitable daily dosages for administration by inhalation are of the order of 0.0001 to 30 mg/kg, typically 0.01 to 10 mg per patient, while for oral administration suitable daily doses are of the order of 0.01 to 100 mg/kg.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e. g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The compounds according to Embodiments 1 to 7.5, exhibit valuable pharmacological properties, e.g. PDGF receptor modulating properties, and are therefore indicated for therapy or for use as research chemicals, e.g. as tool compounds.

Compounds of the invention may be useful in the treatment of an indication selected from respiratory, inflammatory and fibrotic diseases and conditions, for example pulmonary arterial hypertension (PAH).

In a further Embodiment, the disease or disorder is a mast-cell associated disease, a respiratory disease, an inflammatory disorder, irritable bowel syndrome (IBS), inflammatory bowel disease (IBD), an autoimmune disorder, a metabolic disease, a fibrosis disease, a dermatological disease, cariac hypertrophy, cancers of the lung or other tissues in which a PDGFR isoform is mutated, overexpressed or activiated, pulmonary arterial hypertension (PAH) or primary pulmonary hypertension (PPH). In other embodiments of this aspect, the disease is asthma, allergic rhinitis, pulmonary arterial hypertension (PAH), pulmonary fibrosis, hepatic fibrosis, cardiac fibrosis, scleroderma, irritable bowel syndrome (IBS), inflammatory bowel disease (IBD), uticaria, dermatosis, type I diabetes or type II diabetes.

In a further Embodiment, the disease or disorder is mediated by a kinase selected from c-kit, PDGFRα, PDGFRfβ, p38, c-Abl, BCR-abl and c-FMS and the disease or disorder is selected from a mast-cell associated disease, a respiratory disease, an inflammatory disorder, irritable bowel syndrome (IBS), inflammatory bowel disease (IBD), an autoimmune disorder, a metabolic disease, a fibrosis disease, a dermatological disease, pulmonary arterial hypertension (PAH) and primary pulmonary hypertension (PPH).

In certain embodiments of this aspect, the disease is asthma, allergic rhinitis, pulmonary arterial hypertension (PAH), pulmonary fibrosis, hepatic fibrosis, cardiac fibrosis, cardiac hypertrophy, scleroderma, irritable bowel syndrome (IBS), inflammatory bowel disease (IBD), uticaria, dermatosis, type I diabetes or type II diabetes.

Thus, as a further embodiment, the present invention provides the use of a compound according to any one of Embodiments 1 to 7.5 in therapy. In a further embodiment, the therapy is selected from a disease or disorder which may be treated by modulation of a c-kit and/or PDGFR kinase. In another embodiment, the disease or disorder is selected from the afore-mentioned list, suitably pulmonary arterial hypertension.

Thus, as a further embodiment, the present invention provides the use of a compound according to any one of Embodiments 1 to 7.5, in the manufacture of a medicament. In a further embodiment, the medicament is for the treatment of a disease where modulation of a c-kit and/or PDGFR kinase is implicated. In another embodiment, the disease is selected from the afore-mentioned list, suitably pulmonary arterial hypertension (PAH).

In another embodiment, the invention provides a method of treating a disease where modulation of a c-kit and/or PDGFR kinase is implicated, comprising administration of a therapeutically acceptable amount of a compound according to any one of Embodiments 1 to 7.5, or pharmaceutical compositions thereof. In a further embodiment, the medicament is for treatment of a disease which may be treated by inhibition of a c-kit and/or PDGFR kinases. In another embodiment, the disease is selected from a metabolic disease, a fibrotic disease, cardiac hypertrophy, a respiratory disease, an inflammatory disease or disorder, a dermatological disease or an autoimmune disease. In certain embodiments of such methods, the disease or condition is asthma, allergic rhinitis, irritable bowel syndrome (IBS), inflammatory bowel disease (IBD), pulmonary arterial hypertension (PAH), pulmonary fibrosis, liver fibrosis, cardiac fibrosis, scleroderma, urticaria, dermatoses, atopic dermatitis, type I diabetes or type II diabetes.

In another embodiment the disease is selected from a respiratory disease, an inflammatory disorder, irritable bowel syndrome (IBS), inflammatory bowel disease (IBD), a fibrosis disease, pulmonary arterial hypertension (PAH) and primary pulmonary hypertension (PPH). In other embodiments the disease is asthma, pulmonary arterial hypertension (PAH), pulmonary fibrosis, hepatic fibrosis, cardiac fibrosis, or cardiac hypertrophy, suitably pulmonary arterial hypertension (PAH).

In another embodiment, the invention provides a method of treating a disease which is treated by inhibition of the PDGF receptor comprising administration of a therapeutically acceptable amount of a compound according to any one of Embodiments 1 to 7.5. In a further embodiment, the disease is selected from the afore-mentioned list, suitably pulmonary arterial hypertension.

Thus, as a further embodiment, the present invention provides the use of a compound according to any one of Embodiments 1 to 7.5 for the manufacture of a medicament. In a further embodiment, the medicament is for treatment of a disease which may be treated by inhibition of inhibition of c-kit and/or PDGFR kinases. In another embodiment, the disease is selected from the afore-mentioned list, suitably pulmonary arterial hypertension.

The compound of the present invention may be administered either simultaneously with, or before or after, one or more other therapeutic agent. The compound of the present invention may be administered separately, by the same or different route of administration, or together in the same pharmaceutical composition as the other agents. A therapeutic agent is, for example, a chemical compound, peptide, antibody, antibody fragment or nucleic acid, which is therapeutically active or enhances the therapeutic activity when administered to a patient in combination with a compound of the invention.

In one embodiment, the invention provides a product comprising a compound according to any one of Embodiments 1 to 7.5 and at least one other therapeutic agent as a combined preparation for simultaneous, separate or sequential use in therapy. In one embodiment, the therapy is the treatment of a disease or condition mediated by c-kit and/or PDGFR kinases. Products provided as a combined preparation include a composition comprising the compound according to any one of Embodiments 1 to 7.5 and the other therapeutic agent(s) together in the same pharmaceutical composition, or the compound according to any one of Embodiments 1 to 7.5 and the other therapeutic agent(s) in separate form, e.g. in the form of a kit.

In one embodiment, the invention provides a pharmaceutical composition comprising a compound according to any one of Embodiments 1 to 7.5 and another therapeutic agent(s). Optionally, the pharmaceutical composition may comprise a pharmaceutically acceptable carrier, as described above.

In one embodiment, the invention provides a kit comprising two or more separate pharmaceutical compositions, at least one of which contains a compound according to any one of Embodiments 1 to 7.5. In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound according to any one of Embodiments 1 to 7.5 for treating a disease or condition mediated by the PDGF receptor, wherein the medicament is prepared for administration with another therapeutic agent. The invention also provides the use of another therapeutic agent for treating a disease or condition mediated by c-kit and/or PDGFR kinases, wherein the medicament is administered with a compound according to any one of Embodiments 1 to 7.5.

The invention also provides a compound according to any one of Embodiments 1 to 7.5 for use in a method of treating a disease or condition mediated by c-kit and/or PDGFR kinases, wherein the compound according to any one of Embodiments 1 to 7.5 is prepared for administration with another therapeutic agent. The invention also provides another therapeutic agent for use in a method of treating a disease or condition mediated by c-kit and/or PDGFR kinases, wherein the other therapeutic agent is prepared for administration with a compound according to any one of Embodiments 1 to 7.5. The invention also provides a compound according to any one of Embodiments 1 to 7.5 for use in a method of treating a disease or condition mediated by c-kit and/or PDGFR kinases, wherein the compound according to any one of Embodiments 1 to 7.5 is administered with another therapeutic agent. The invention also provides another therapeutic agent for use in a method of treating a disease or condition mediated by c-kit and/or PDGFR kinases, wherein the other therapeutic agent is administered with a compound according to any one of Embodiments 1 to 7.45.

The invention also provides the use of a compound according to any one of Embodiments 1 to 7.5 for treating a disease or condition mediated by c-kit and/or PDGFR kinases, wherein the patient has previously (e.g. within 24 hours) been treated with another therapeutic agent. The invention also provides the use of another therapeutic agent for treating a disease or condition mediated by c-kit and/or PDGFR kinases wherein the patient has previously (e.g. within 24 hours) been treated with a compound according to any one of Embodiments 1 to 7.5.

In one embodiment, the other therapeutic agent is selected from:

organic nitrates and NO-donors, such as sodium nitroprusside, nitroglycerin, isosorbide mononitrate, isosorbide dinitrate, molsidomine or SIN-1, and inhalational NO; compounds that inhibit the degradation of cyclic guanosine monophosphate (cGMP) and/or cyclic adenosine monophosphate (cAMP), such as inhibitors of phosphodiesterases (PDE) 1, 2, 3, 4 and/or 5, especially PDE 5 inhibitors such as sildenafil, vardenafil and tadalafil; NO-independent, but haem-dependent stimulators of guanylate cyclase, such as in particular the compounds described in WO 00/06568, WO 00/06569, WO 02/42301 and WO 03/095451; NO- and haem-independent activators of guanylate cyclase, such as in particular the compounds described in WO 01/19355, WO 01/19776, WO 01/19778, WO 01/19780, WO 02/070462 and WO 02/070510; compounds which inhibit human neutrophilic elastase, such as sivelestat or DX-890 (Reltran); compounds inhibiting the signal transduction cascade, such as tyrosine kinase and/or serine/threonine kinase inhibitors, in particular imatinib, gefitinib, erlotinib, sorafenib and sunitinib; compounds influencing the energy metabolism of the heart, for example and preferably etomoxir, dichloroacetate, ranolazine or trimetazidine; antithrombotic agents, for example and preferably from the group comprising platelet aggregation inhibitors, anticoagulants or profibrinolytic substances; active substances for lowering blood pressure, for example and preferably from the group comprising calcium antagonists, angiotensin II antagonists, ACE inhibitors, endothelin antagonists, renin inhibitors, aldosterone synthase inhibitors, alpha receptor blockers, beta receptor blockers, mineralocorticoid receptor antagonists, Rho-kinase inhibitors and diuretics; and/or active substances that modify lipid metabolism, for example and preferably from the group comprising thyroid receptor agonists, inhibitors of cholesterol synthesis, for example and preferably HMG-CoA-reductase inhibitors or inhibitors of squalene synthesis, ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbers, bile acid reabsorption inhibitors and lipoprotein(a) antagonists, particularly in the treatment of PAH or diseases and disorders such as those mentioned hereinbefore, e.g., as potentiators of therapeutic activity of such drugs or as a means of reducing required dosaging or potential side effects of such drugs.

In particular, an embodiment of this invention is a pharmaceutical combination comprising the compounds according to any one of Embodiments 1 to 7.5 and a second agent wherein the second agent is a PDEV inhibitor or neutral endopeptidase inhibitor.

The compounds according to any one of Embodiments 1 to 7.5 may be mixed with a second agent in a fixed pharmaceutical composition or it may be administered separately, before, simultaneously with or after the other drug substance.

Other useful combinations of the compounds according to any one of Embodiments 1 to 7.5 with anti-inflammatory drugs are those with antagonists of chemokine receptors, e.g., CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists, such as Schering-Plough antagonists SC-351125, SCH-55700 and SCH-D; Takeda antagonists, such as N-[[4-[[[6,7-dihydro-2-(4-methyl-phenyl)-5H-benzo-cyclohepten-8-yl]carbonyl]

amino]phenyl]-methyl]tetrahydro-N,N-dimethyl-2H-pyran-4-amin-ium chloride (TAK-770); and CCR-5 antagonists described in U.S. Pat. No. 6,166,037 (particularly claims 18 and 19), WO 00/66558 (particularly claim 8), WO 00/66559 (particularly claim 9), WO 04/018425 and WO 04/026873.

Suitable anti-inflammatory drugs include steroids, in particular, glucocorticosteroids, such as budesonide, beclamethasone dipropionate, fluticasone propionate, ciclesonide or mometasone furoate, or steroids described in WO 02/88167, WO 02/12266, WO 02/100879, WO 02/00679 (especially those of Examples 3, 11, 14, 17, 19, 26, 34, 37, 39, 51, 60, 67, 72, 73, 90, 99 and 101), WO 03/35668, WO 03/48181, WO 03/62259, WO 03/64445, WO 03/72592, WO 04/39827 and WO 04/66920; non-steroidal glucocorticoid receptor agonists, such as those described in DE 10261874, WO 00/00531, WO 02/10143, WO 03/82280, WO 03/82787, WO 03/86294, WO 03/104195, WO 03/101932, WO 04/05229, WO 04/18429, WO 04/19935 and WO 04/26248; LTD4 antagonists, such as montelukast and zafirlukast; PDE4 inhibitors, such as cilomilast (Ariflo® GlaxoSmithKline), Roflumilast (Byk Gulden),V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID™ CC-10004 (Celgene), VM554/UM565 (Vernalis), T-440 (Tanabe), KW-4490 (Kyowa Hakko Kogyo), and those disclosed in WO 92/19594, WO 93/19749, WO 93/19750, WO 93/19751, WO 98/18796, WO 99/16766, WO 01/13953, WO 03/104204, WO 03/104205, WO 03/39544, WO 04/000814, WO 04/000839, WO 04/005258, WO 04/018450, WO 04/018451, WO 04/018457, WO 04/018465, WO 04/018431, WO 04/018449, WO 04/018450, WO 04/018451, WO 04/018457, WO 04/018465, WO 04/019944, WO 04/019945, WO 04/045607 and WO 04/037805; adenosine A2B receptor antagonists such as those described in WO 02/42298; and beta-2 adrenoceptor agonists, such as albuterol (salbutamol), metaproterenol, terbutaline, salmeterol fenoterol, procaterol, and especially, formoterol, carmoterol and pharmaceutically acceptable salts thereof, and compounds (in free or salt or solvate form) of formula (I) of WO 0075114, which document is incorporated herein by reference, preferably indacaterol and pharmaceutically acceptable salts thereof, as well as compounds (in free or salt or solvate form) of formula (I) of WO 04/16601, and also compounds of EP 1440966, JP 05025045, WO 93/18007, WO 99/64035, U.S. Pat. No. 2002/0055651, WO 01/42193, WO 01/83462, WO 02/66422, WO 02/70490, WO 02/76933, WO 03/24439, WO 03/42160, WO 03/42164, WO 03/72539, WO 03/91204, WO 03/99764, WO 04/16578, WO 04/22547, WO 04/32921, WO 04/33412, WO 04/37768, WO 04/37773, WO 04/37807, WO 04/39762, WO 04/39766, WO 04/45618, WO 04/46083, WO 04/80964, WO 04/108765 and WO 04/108676.

Suitable bronchodilatory drugs include anticholinergic or antimuscarinic agents, in particular, ipratropium bromide, oxitropium bromide, tiotropium salts and CHF 4226 (Chiesi), and glycopyrrolate, but also those described in EP 424021, U.S. Pat. No. 3,714,357, U.S. Pat. No. 5,171,744, WO 01/04118, WO 02/00652, WO 02/51841, WO 02/53564, WO 03/00840, WO 03/33495, WO 03/53966, WO 03/87094, WO 04/018422 and WO 04/05285.

Suitable dual anti-inflammatory and bronchodilatory drugs include dual beta-2 adrenoceptor agonist/muscarinic antagonists such as those disclosed in U.S. 2004/0167167, WO 04/74246 and WO 04/74812.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine, as well as those disclosed in JP 2004107299, WO 03/099807 and WO 04/026841.

Accordingly, the invention includes as a further aspect a combination of PDGFR inhibitor with agents that inhibit ALK5 and/or ALK4 phosphorylation of Smad2 and Smad3.

Accordingly, the invention includes as a further aspect a combination of PDGFR inhibitor with second agents that are Rho-kinase inhibitors. Accordingly, the invention includes as a further aspect a combination of a compound according to any one of Embodiments 1 to 7.5 with second agents that are TPH1 antagonists.

Accordingly, the invention includes as a further aspect a combination of a compound according to any one of Embodiments 1 to 7.5 with second agents that are IP receptor agonist.

Accordingly, the invention includes as a further aspect a combination of a compound according to any one of Embodiments 1 to 7.5 with second agents that are multi-kinase inhibitors, such as imatinib mysilate (Gleevec®) or nilotinib. Imatinib functions as a specific inhibitor of a number of tyrosine kinase enzymes. It occupies the TK active site, leading to a decrease in activity. TK enzymes in the body, include the insulin receptor. Imatinib is specific for the TK domain in the Abelson proto-oncogene, c-kit and PDGF-R (platelet-derived growth factor receptor).

The following examples are intended to illustrate the invention and are not to be construed as being limitations thereon.

EXAMPLES

General Conditions

Mass spectra were run on LCMS systems using electrospray ionization. These were either Agilent 1100 HPLC/Micromass Platform Mass Spectrometer combinations or Waters Acquity UPLC with SQD Mass Spectrometer. [M+H]$^+$ refers to mono-isotopic molecular weights.

NMR spectra were run on open access Bruker AVANCE 400 NMR spectrometers using ICON-NMR. Spectra were measured at 298K and were referenced using the solvent peak.

The following examples are intended to illustrate the invention and are not to be construed as being limitations thereon. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art. If not defined, the terms have their generally accepted meanings.

Abbreviations
aq. aqueous
br broad
d doublet
DCM dichloromethane
DMF N,N-dimethylformamide
DMAC dimethylacetamide
DMSO dimethylsulfoxide
EtOAc ethyl acetate
hr hour
HOBt hydroxybenzotriazole
HPLC high pressure liquid chromatography
LC-MS liquid chromatography and mass spectrometry
MeOH methanol MS mass spectrometry
m multiplet
min minutes
ml milliliter(s)
m/z mass to charge ratio
NMR nuclear magnetic resonance
ppm parts per million
Rt retention time
RT room temperature
s singlet
t triplet
TEA triethylamine
TBD 2,3,4,6,7,8-hexahydro-1H-pyrimido[1,2-a]pyrimidine
THF tetrahydrofuran Referring to the examples that follow, compounds of the preferred embodiments were synthesized using the methods described herein, or other methods, which are known in the art.

The various starting materials, intermediates, and compounds of the preferred embodiments may be isolated and purified, where appropriate, using conventional techniques such as precipitation, filtration, crystallization, evaporation, distillation, and chromatography. Unless otherwise stated, all starting materials are obtained from commercial suppliers and used without further purification. Salts may be prepared from compounds by known salt-forming procedures.

It should be understood that the organic compounds according to the preferred embodiments may exhibit the phenomenon of tautomerism. As the chemical structures within this specification can only represent one of the possible tautomeric forms, it should be understood that the preferred embodiments encompasses any tautomeric form of the drawn structure.

Unless indicated otherwise, the analytical HPLC conditions are as follows:
Method 10 min LC
Column Aglient, Poroshell 120 SB-C18 2.7 µm 3.0×50mm
Column Temp. 30° C.
Eluents B: H$_2$O, C: acetonitrile, both containing 0.1% Formic acid
Flow Rate 0.8 ml/min
Gradient 0.50 min 5% C; 5% to 95% C in 6.50 min, 95% to 5% C in 3 min
Method 10 min LC_v003
Column Waters BEH C18 50×2.1 mm, 1.7 m
Column Temp 50° C.
Eluents A: H$_2$O, B: acetonitrile, both containing 0.1% TFA
Flow Rate 0.8 mL/min
Gradient 0.20 min 5% B; 5% to 95% B in 7.80 min, 1.00 min 95% B
2 min Low pH
Column: Waters Acquity CSH 1.7 µm, 2.1×50mm
Column Temp 50° C.
Mobile Phase: A: Water+0.1% Formic Acid, B: Acetonitrile+0.1% Formic Acid
Flow rate: 1.0 mL/min
Gradient: 0.0min 5% B, 0.2-1.3min 5-98% B, 1.3-1.55min 98% B, 1.55-1.6min 98-5% B
Method 2 min LC_v003
Column Waters BEH C18 50×2.1 mm, 1.7 mm
Column Temp 50° C.
Eluents A: H$_2$O, B: acetonitrile, both containing 0.1% TFA
Flow Rate 0.8 mL/min
Gradient 0.20 min 5% B; 5% to 95% B in 1.30 min, 0.25 min 95% B
This method runs on Acquity A, B, and C
X-Ray Powder Diffraction Measurements X-ray powder diffraction (PXRD) data were obtained using a Bruker D8 Advance (Cu Kα) with Lynxeye detector in reflection mode. 2Th/Th locked.

One of ordinary skill in the art will appreciate that an X-ray diffraction pattern may be obtained with a measurement error that is dependent upon the measurement conditions employed. In particular, it is generally known that intensities in a X-ray diffraction pattern may fluctuate depending upon measurement conditions employed. It should be further understood that relative intensities may also vary depending upon experimental conditions and, accordingly, the exact order of intensity should not be taken into account. Additionally, a measurement error of diffraction angle for a conventional X-ray diffraction pattern is typically about 5% or less, and such degree of measurement error should be taken into account as pertaining to the aforementioned diffraction angles.

Measurement Parameters
Instrument: Bruker D8 Advance
Radiation: CuKα
Generator mA: 40 mA
Generator kV: 30 kV
Detector: Lynxeye
Measurement range: 2-40° 2 theta
Scan rate (continuous scan): 0.3 s/step
Step size: 0.017°
Divergence slit: V12 (variable)
Soller slit: 2.5°
Lynxeye Iris: 8 mm
Measurement mode: Reflection
Sample holder: Low-background silicon sample holder (0.5 mm depth)
Temperature: about 25° C. (RT)
Differential Scanning Calorimetry (DSC)

Differential scanning calorimetry (DSC) data were obtained using a Mettler-Toledo DSC 1. Powder samples were placed in pierced aluminium crucibles for data collection. Data was collected by heating from 30° C. to 300° C. at a heating rate of 20° C./min, under a nitrogen flow of 45 mL/min.

The heat flow, which was normalized by a sample weight, was plotted versus the measured sample temperature. The data were reported in units of watts/gram ("W/g"). The plot was made with the endothermic peaks pointing upwards (unless indicated otherwise in the figure). The endothermic melt peak was evaluated for extrapolated onset temperature, peak temperature, and heat of fusion in this analysis.

Example 1

N-(5-(2-(2,6-cis-Dimethylpiperidin-1-yl)ethylcarbamoyl)-2-fluorophenyl)-7-(1-methyl-1H-pyrazol-5-yl)imidazo[1,2-a]pyridine-3-carboxamide

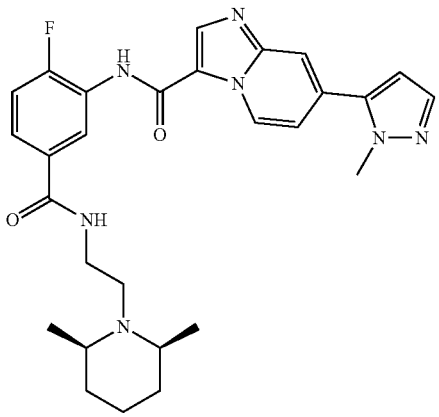 [SMILES: C[C@@H]1CCC[C@H](C)N1CCNC(=O)c1ccc(F)c(NC(=O)c2cnc3cc(-c4ccnn4C)ccn23)c1]

PdCl$_2$(dppf).CH$_2$Cl$_2$ adduct (39.5 mg, 0.048 mmol) was added to a mixture comprising 1-methyl-3-(4,4,5,5-tetramethyl-1,3,2-dioxaborolan-2-yl)-1H-pyrazole (commercially available) (212 mg, 1.017 mmol), 7-bromo-N-(5-(2-(2,6-cis-dimethylpiperidin-1-yl)ethylcarbamoyl)-2-fluorophenyl) imidazo[1,2-a]pyridine-3-carboxamide (Intermediate 3) (500 mg, 0.968 mmol), Cs$_2$CO$_3$ (1262 mg, 3.87 mmol) in 1,2-dimethoxyethane (10 ml) and water (4.29 ml). The mixture was degassed thoroughly refilling with nitrogen (×3). The mixture was heated using microwave radiation at 100° C. for 1 hour. The water was removed by pipette and the organic portion was concentrated in vacuo. The residue was dissolved in MeOH and dry loaded onto silica. The crude product was purified by chromatography on silica eluting with 0-20% MeOH in DCM to afford the title compound. Rt 1.91 mins; MS m/z 518.40 [M+H]+; Method 10 min LC_v003

1H NMR (400 MHz, DMSO-d6) δ 10.7 (1H, s), 10.0 (1/2H, m), 9.5 (1H, d), 9 (1H, t), 8.8 (1H, s), 8.2 (1H, m) 8.1 (1H, s), 7.6 (1H, s), 7.5 (2H, d), 6.6 (1H, s) 4 (3H, s), 3.6 (2H, m), 3.4 (2H, m), 3.3 (2H, m), 3.1 (1H, m), 1.9 (1H, m), 1.6 (2H, m), 1.5 (2H, m), 1.4 (4H, d), 1.3 (2H, d)

Alternatively, N-(5-(2-(2,6-cis-dimethylpiperidin-1-yl)ethylcarbamoyl)-2-fluorophenyl)-7-(1-methyl-1H-pyrazol-5-yl)imidazo[1,2-a]pyridine-3-carboxamide was prepared according to the following procedure:

Step 1: 3-[(7-Bromo-imidazo[1,2-a]pyridine-3-carbonyl)-amino]-4-fluoro-benzoic acid methyl ester To the solution of compound 7-bromoimidazo[1,2-a]pyridine-3-carboxylic acid (Intermediate 1) (1.26 Kg, 5.23 mol) in DMAC (15 L) was added dropwise SOCl$_2$ (1.86 kg, 15.6 mol) at 10° C. in 30 min. To the resulting mixture warmed to 20° C. was added compound methyl 3-amino-4-fluorobenzoate (884 g, 5.23 mol) in DMAC (3.0 L) over 30 min. After addition, the reaction temperature went up to 30° C. HPLC showed the reaction went to completion within 5 min. To the reaction mixture was added water (20 L) over 20 min. The mixture was filtered and dried under vacuum to afford the title compound as a white solid;

$^1$H NMR (400 MHz, DMSO-d6) δ 3.87 (s, 3 H) 7.57 (dd, J=7.28, 2.01 Hz, 1 H) 7.51 (dd, J=10.16, 8.66 Hz, 1 H) 7.90 (td, J=4.33, 2.38 Hz, 1 H) 8.29 (m, 2H) 8.90 (s, 1 H) 9.43 (d, J=7.53 Hz, 1 H) 10.78 (s, 1 H)

Rt 6.90 mins; MS m/z 394.0 {M+H}+; Method 10 min LC

Step 2: 4-Fluoro-3-{[7-(2-methyl-2H-pyrazol-3-yl)-imidazo[1,2-a]pyridine-3-carbonyl]-amino}-benzoic acid 3-[(7-Bromo-imidazo[1,2-a]pyridine-3-carbonyl)-amino]-4-fluoro-benzoic acid methyl ester (step 1) (1200 g, 3.060 mol), 1-methyl-3-(4,4,5,5-tetramethyl-1,3,2-dioxaborolan-2-yl)-1H-pyrazole (commercially available) (764 g, 3.67 mol), PdCl$_2$(dppf)•CH$_2$Cl$_2$ (75.0 g, 91.8 mmol) in dioxane (10 L) and aqueous Na$_2$CO$_3$ (2 N, 4.6 L) were heated to reflux for 6 hr. The reaction mixture was cooled to 50° C. and filtered. The filtrate was heated to reflux, to which was added AcOH (600 g, 10.0 mol) was added dropwise. During the course of addition solids came out of solution to give pale pink slurry. After addition the mixture was slowly cooled to RT and filtered. To the filter cake was added dioxane (20 L) followed by heating to reflux to obtain a solution. The solution was cooled to RT and filtered to provide the title compound as a white solid;

$^1$H NMR (400 MHz, DMSO-d$_6$) δ 4.00 (s, 3 H) 6.67 (s, 1 H) 7.46 (t, J=9.41 Hz, 1 H) 7.40 (d, J=7.03 Hz, 1 H) 7.54 (s, 1 H) 7.85 (d, J=2.26 Hz, 1 H) 7.99 (s, 1 H) 8.28 (d, J=6.27 Hz, 1 H) 8.67 (s, 1 H) 9.47 (d, J=7.03Hz, 1 H) 10.35 (s, 1 H).

Rt 5.40 mins; MS m/z 380.1 {M+H}+; Method 10 min LC

Step 3: N-(5-(2-(2,6-cis-dimethylpiperidin-1-yl)ethylcarbamoyl)-2-fluorophenyl)-7-(1-methyl-1H-pyrazol-5-yl)imidazo[1,2-a]pyridine-3-carboxamide 4-Fluoro-3-{[7-(2-methyl-2H-pyrazol-3-yl)-imidazo[1,2-a]pyridine-3-carbonyl]amino}-benzoic acid (step 2) (450 g, 1.19 mol), EDC.HCl (454.8 g, 2.372 mol) and HOBt (181.6 g, 1.186 mol) in DMF (3.2 L) at 25° C. were stirred for 1.5 hr. The reaction was monitored by HPLC. To the reaction mixture was dropwise added cis 2-(2,6-dimethyl-piperidin-1-yl)-ethylamine (222.5 g, 1.423 mol) over 10 min and stirring continued for 30 min. To the reaction mixture was dropwise an aqueous solution of Na$_2$CO$_3$ (5%, 6 L) over 120 min and the resulting solid was collected by filtration and washed with water (5 L). To the solid was added ethanol (5 L) followed by heating to 70° C. to obtain a clear solution. Water (1.5 L) was dropwise added at 70° C. and stirred for 30 min. The clear solution was slowly cooled to 25° C. over 2 hr. The solid was filtered, washed with ethanol (500 mL) and dried under vacuum at 50° C. overnight to afford the title compound as a white solid;

$^1$H NMR (400 MHz, DMSO-d$_6$) δ 1.03-1.19 (m, 3 H) 1.10 (d, J=6.02 Hz, 6 H) 1.55 (br. s., 1 H) 1.50 (d, J=12.30 Hz, 2 H) 2.42 (br. s., 2 H) 2.71 (br. s., 2 H) 3.27 (d, J=5.77 Hz, 2 H) 4.00 (s, 3 H) 6.60 (s, 1H) 7.41 (d, J=6.02 Hz, 2 H) 7.54 (s, 1 H) 7.77 (s, 1 H) 8.00 (s, 1 H) 8.14 (d, 1 H) 8.54 (s, 1 H) 8.67 (s, 1 H) 9.48 (d, 1 H) 10.35 (s, 1 H).

Rt 4.80 mins; MS m/z 518.2 {M+H}+; Method 10 min LC

Example 2

N-(5-(2-(2,2-dimethylpyrrolidin-1-yl)ethylcarbamoyl)-2-methylpyridin-3-yl)-6-(1-methyl-1H-pyrazol-4-yl)pyrazolo[1,5-a]pyridine-3-carboxamide

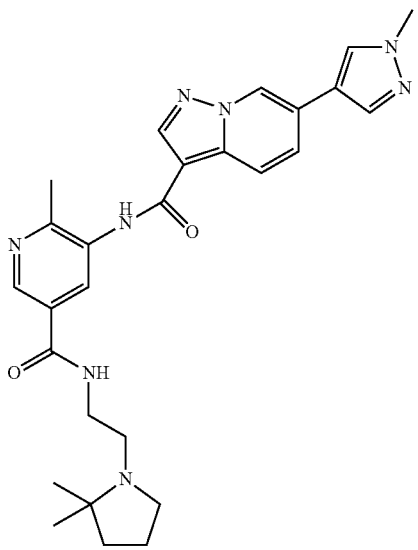 [SMILES: Cc1ncc(C(=O)NCCN2CCCC2(C)C)cc1NC(=O)c1cnn2cc(-c3cnn(C)c3)ccc12]

Step 1: Methyl 5-(6-bromopyrazolo[1,5-a]pyridine-3-carboxamido)-6-methylnicotinate 6-Bromopyrazolo[1,5-a]pyridine-3-carboxylic acid (7.71 g, 32.0 mmol) in toluene (80 ml) was treated with thionyl chloride (18.67 ml, 256 mmol) and was heated to 110° C. for 6 hr. The solvent was removed in vacuo and the residue was treated with pyridine (80 ml), methyl 5-amino-6-methylnicotinate (4.25 g, 25.6 mmol) and oven dried molecular sieves. The reaction mixture was stirred at RT overnight and then treated with MeOH (250 ml). The resulting suspension was removed by filtration. The filtrate was triturated with methanol and the solid produced was isolated to afford the title compound;

LCMS: Rt 0.91 mins; MS m/z 391.4 [M+H]+; Method 2 min Low pH

Step 2: 6-Methyl-5-(6-(1-methyl-1H-pyrazol-4-yl)pyrazolo[1,5-a]pyridine-3-carboxamido)nicotinic acid Methyl 5-(6-bromopyrazolo[1,5-a]pyridine-3-carboxamido)-6-methylnicotinate (step 1) (7 g, 17.99 mmol), 1-methyl-4-(4,4,5,5-tetramethyl-1,3,2-dioxaborolan-2-yl)-1H-pyrazole (4.49 g, 21.58 mmol) and cesium carbonate (23.44 g, 71.9 mmol) were stirred in 1,2-dimethoxyethane (60 ml) and water (25.00 ml). The mixture was degassed thoroughly refilling with nitrogen. PdCl$_2$(dppf).CH$_2$Cl$_2$ adduct (0.350 g, 0.429 mmol) was added and the mixture was degassed thoroughly refilling with nitrogen, The mixture was stirred at 100° C. for 7 hrs and then cooled to 50° C. and filtered through glass-fiber paper. The filtrate was acidified to pH 5 by the addition of 2M HCl and filtered. The foam residue was dissolved in DCM/MeOH (1:1) and azeotroped with toluene (×2). The resulting solid was dried in a vacuum oven to afford the title compound;

LCMS: Rt 0.69 mins; MS m/z 377.5 [M+H]+; Method 2 min Low pH

Step 3: N-(5-(2-(2,2-Dimethylpyrrolidin-1-yl)ethylcarbamoyl)-2-methylpyridin-3-yl)-6-(1-methyl-1H-pyrazol-4-yl)pyrazolo[1,5-a]pyridine-3-carboxamide 6-Methyl-5-(6-(1-methyl-1H-pyrazol-4-yl)pyrazolo[1,5-a]pyridine-3-carboxamido)nicotinic acid (6.6 g, 1.1 equiv) and 2-(2,2-dimethylpyrrolidin-1-yl)ethanamine (2.397 g, 11.14 mmol) were combined in DMF (100 ml) and treated with DIPEA (8.34 ml, 47.7 mmol) followed by HATU (4.44 g, 11.67 mmol). After stirring at RT for 90 mins, the mixture was partitioned between water (1 L) and EtOAc (750 ml). The resulting suspension was removed by filtration and the organic portion was washed with aqueous sodium bicarbonate, 0.5M lithium chloride, brine, dried MgSO$_4$, filtered and evaporated to dryness. Purification by chromatography on silica eluting with 0-20% 2M NH$_3$ in MeOH/TBME afforded residue which was recrystallised from acetone to afford the title compound;

LCMS: Rt 0.61 mins; MS m/z 501 [M+H]+; Method 2 min Low pH

1H NMR (400 MHz, DMSO) δ 9.75 (1H, s), 9.15 (1H, s), 8.75 (2H, m), 8.58 (1H, t), 8.32 (1H, s), 8.25 (1H, s), 8.21 (1H, d), 8.07 (1H, s), 7.82 (1H, d), 3.89 (3H, s), 3.34 (4H, m), 2.76 (2H, t), 2.56 (3H, s), 1.69 (2H, m), 1.53 (2H, m) 0.92 (6H, s)

Example 3

N-(5-(2-(2,6-cis-Dimethylpiperidin-1-yl)ethylcarbamoyl)-2-fluorophenyl)-7-(1-methyl-1H-pyrazol-5-yl)imidazo[1,2-a]pyridine-3-carboxamide Saccharinate 515 mg of N-(5-(2-(2,6-cis-Dimethylpiperidin-1-yl)ethylcarbamoyl)-2-fluorophenyl)-7-(1-methyl-1H-pyrazol-5-yl)imidazo[1,2-a]pyridine-3-carboxamide (free base) was weighed out into 100 mL reaction vessels and 184.08 mg of saccharin was added to give a 1:1 molar ratio of compound and counter ion. 20 mL of ethyl acetate was added to the solids to produce a slurry.

Salt formation was attempted using temperature cycling and the PolyBLOCK PB4 system. The PolyBLOCK chamber was set to heat from 5° C. to 50° C. at 5° C./min then cool at 0.5° C./min until it reached 5° C. with a further hold for 30 minutes. The cycle then repeated. Stirring with a magnetic stirrer occurred throughout at 500 rpm.

After 48 hours cycling the vessel was removed from the temperature cycling program. Isolation of the solids was achieved by vacuum filtration where the mother liquors were retained and the remaining cake was left at 45° C. under vacuum for ~60 hours. The solid were analysed subsequently by XRPD to assess salt formation and compared to previous screening batches. The purity of the compound was also checked via UPLC.

XRPD

| Angle 2-Theta ° +/− 0.2° 2theta | d value Angstrom | Intensity % |
|---|---|---|
| 4.9 | 18.12758 | 2 |
| 9.3 | 9.50280 | 5 |
| 9.9 | 8.96661 | 11 |
| 10.1 | 8.78292 | 13 |
| 11.1 | 7.98588 | 11 |
| 12.3 | 7.21201 | 19 |
| 12.8 | 6.91369 | 19 |
| 14.5 | 6.11666 | 7 |
| 15.0 | 5.91102 | 92 |
| 15.9 | 5.56896 | 7 |
| 16.4 | 5.39068 | 23 |
| 16.7 | 5.31106 | 16 |
| 17.1 | 5.18299 | 42 |
| 17.3 | 5.13503 | 29 |
| 17.7 | 5.00087 | 34 |
| 18.3 | 4.83460 | 7 |
| 18.9 | 4.70147 | 79 |
| 19.1 | 4.63752 | 30 |
| 19.5 | 4.55563 | 35 |
| 19.8 | 4.48631 | 58 |
| 20.1 | 4.42285 | 13 |
| 20.4 | 4.35816 | 32 |
| 21.1 | 4.21067 | 15 |
| 21.5 | 4.12906 | 100 |
| 22.2 | 3.99354 | 28 |
| 22.7 | 3.90781 | 11 |
| 23.2 | 3.82808 | 17 |
| 23.7 | 3.75456 | 19 |
| 24.7 | 3.60267 | 9 |
| 25.1 | 3.54627 | 95 |
| 25.4 | 3.49930 | 77 |
| 25.8 | 3.44774 | 49 |
| 26.5 | 3.35811 | 14 |
| 26.8 | 3.32925 | 29 |
| 27.1 | 3.29340 | 22 |
| 27.5 | 3.24448 | 14 |
| 28.0 | 3.18192 | 10 |
| 28.3 | 3.15307 | 12 |
| 28.6 | 3.12164 | 28 |
| 29.1 | 3.06564 | 13 |
| 29.6 | 3.01745 | 13 |
| 30.0 | 2.97546 | 17 |
| 30.4 | 2.93402 | 13 |
| 30.6 | 2.91740 | 14 |
| 31.6 | 2.83284 | 9 |
| 31.7 | 2.81955 | 11 |
| 32.2 | 2.77633 | 6 |
| 32.6 | 2.74236 | 7 |
| 33.0 | 2.70923 | 6 |
| 33.4 | 2.68056 | 16 |
| 33.7 | 2.65702 | 10 |
| 34.3 | 2.61196 | 10 |
| 35.0 | 2.55850 | 10 |
| 35.6 | 2.51803 | 16 |
| 36.0 | 2.49360 | 9 |
| 36.6 | 2.45286 | 9 |
| 37.3 | 2.40852 | 7 |
| 37.6 | 2.39106 | 9 |
| 38.0 | 2.36624 | 10 |
| 38.5 | 2.33892 | 11 |
| 39.0 | 2.30737 | 8 |
| 39.6 | 2.27216 | 15 |

Differential Scanning Calorimetry (DSC) Data

The DSC curve shows an endotherm with an onset temperature of 220.1° C. which is related to the melting of the sample (melting endotherm).

Example 4

N-(5-(2-(2,6-cis-Dimethylpiperidin-1-yl)ethylcarbamoyl)-2-fluorophenyl)-7-(1-methyl-1H-pyrazol-5-yl)imidazo[1,2-a]pyridine-3-carboxamide Maleate 1000.15 mg of N-(5-(2-(2,6-cis-Dimethylpiperidin-1-yl)ethylcarbamoyl)-2-fluorophenyl)-7-(1-methyl-1H-pyrazol-5-yl)imidazo[1,2-a]pyridine-3-carboxamide (free base) was weighed out into 100 mL reaction vessels and 226.52 mg of maleic acid was added to give a 1:1 molar ratio of compound and counter ion. 40 mL of ethyl acetate was added to the solids to produce a slurry.

Salt formation was attempted using temperature cycling and the PolyBLOCK PB4 system. The PolyBLOCK chamber was set to heat from 5° C. to 50° C. at 5° C./min then cool at 0.5° C./min until it reached 5° C. with a further hold for 30 minutes. The cycle then repeated. Stirring with a magnetic stirrer occurred throughout at 500 rpm.

After 48 hours cycling the vessel was removed from the temperature cycling program. Isolation of the solids was achieved by vacuum filtration where the mother liquors were retained and the remaining cake was left at 45° C. under vacuum for ~60 hours. The solid were analysed subsequently by XRPD to assess salt formation and compared to previous screening batches. The purity of the compound was also checked via UPLC.

XRPD

| Angle 2-Theta ° +/− 0.2° 2theta | d value Angstrom | Intensity % |
|---|---|---|
| 3.5 | 25.09039 | 43 |
| 10.7 | 8.28386 | 8 |
| 11.4 | 7.77625 | 28 |
| 11.6 | 7.61379 | 21 |
| 12.7 | 6.95934 | 11 |
| 13.0 | 6.80858 | 10 |
| 14.2 | 6.21865 | 77 |
| 14.6 | 6.07888 | 32 |
| 15.1 | 5.85804 | 24 |
| 16.0 | 5.54820 | 15 |
| 16.6 | 5.32854 | 21 |
| 17.4 | 5.10164 | 62 |
| 18.0 | 4.93485 | 15 |
| 18.7 | 4.75118 | 13 |
| 19.6 | 4.52333 | 37 |
| 20.8 | 4.27730 | 19 |
| 21.7 | 4.08845 | 13 |
| 22.1 | 4.01684 | 21 |
| 22.9 | 3.88625 | 27 |
| 23.2 | 3.83659 | 45 |
| 23.6 | 3.75968 | 37 |
| 24.3 | 3.66621 | 55 |
| 24.9 | 3.57247 | 64 |
| 25.7 | 3.46711 | 100 |
| 26.2 | 3.40117 | 25 |
| 26.9 | 3.31113 | 40 |
| 27.5 | 3.23937 | 17 |
| 28.4 | 3.14369 | 13 |
| 28.7 | 3.10499 | 16 |
| 30.5 | 2.92882 | 20 |
| 31.1 | 2.87399 | 16 |
| 32.2 | 2.77460 | 15 |
| 32.9 | 2.72109 | 13 |
| 33.7 | 2.65845 | 14 |
| 34.3 | 2.60865 | 13 |
| 35.3 | 2.54378 | 11 |
| 35.4 | 2.53308 | 12 |
| 35.6 | 2.52069 | 13 |

-continued

| Angle 2-Theta °<br>+/− 0.2° 2theta | d value Angstrom | Intensity % |
|---|---|---|
| 36.3 | 2.47473 | 15 |
| 37.2 | 2.41278 | 11 |
| 37.3 | 2.40855 | 11 |
| 38.0 | 2.36477 | 12 |
| 39.7 | 2.26812 | 12 |

Differential Scanning Calorimetry (DSC) Data

The DSC curve shows three thermal events. The first endotherm with an onset temperature of 51.6° C. is likely attributable to the evaporation of residual solvent in the sample and may not be reproducible with other samples. The second endotherm with an onset temperature of 182.4° C. is related to the melting of the sample and subsequent decomposition. The third endotherm with an onset temperature of 25.8° C. is related to further decomposition of the material at higher temperatures.

Example 5

N-(5-(2-(2,2-dimethylpyrrolidin-1-yl)ethylcarbamoyl)-2-methylpyridin-3-yl)-6-(1-methyl-1H-pyrazol-4-yl)pyrazolo[5-a]pyridine-3-carboxamide L-Tartrate Method A: 1000 μL of 95% IPA was added to 100 mg N-(5-(2-(2,2-dimethylpyrrolidin-1-yl)ethylcarbamoyl)-2-methylpyridin-3-yl)-6-(1-methyl-1H-pyrazol-4-yl)pyrazolo[1,5-a]pyridine-3-carboxamide (free base) at 55° C. to dissolve the free form and 1000 μL of 0.2M L-tartaric acid in acetone (at 1:1 molar ratio) was added dropwise. Solid precipitation was observed when 500~600 μL tartaric acid solution was added. The slurry was stirring at 55° C. for 60 minutes and then cooled at about 0.3° C./min to 5° C. where it was held for 1 hour. Cycle was repeated 3 times. The heating rate to 55° C. was 1° C./min and finally hold at 5° C. Solid precipitate was obtained after holding the suspension at 5° C. for over 1 hour after completion of the cycle. The resulting solid was collected by filtration and dried at 40° C. under vacuum for 24 hours. The yield was approximately 79%.

Method B: N-(5-(2-(2,2-dimethylpyrrolidin-1-yl)ethylcarbamoyl)-2-methylpyridin-3-yl)-6-(1-methyl-1H-pyrazol-4-yl)pyrazolo[1,5-a]pyridine-3-carboxamide (500 mg) and 150.7 mg L-tartaric acid (99.5%) were placed in a glass vial and methanol (3 ml) added. The mixture was heated until complete dissolution and allowed to cool to room temperature under stirring. Precipitation occurred at 28° C. and a yellowish suspension was formed. The suspension was stirred at room temperature for approximately 22 h, filtered, washed with methanol (0.5 ml) and dried for 24 h in a vacuum oven at room temperature to isolate the title product as an off-white powder (521.4 mg).

Method C: Alternatively, a suspension of N-(5-(2-(2,2-dimethylpyrrolidin-1-yl)ethylcarbamoyl)-2-methylpyridin-3-yl)-6-(1-methyl-1H-pyrazol-4-yl)pyrazolo[1,5-a]pyridine-3-carboxamide L-tartrate in methanol was seeded with N-(5-(2-(2,2-dimethylpyrrolidin-1-yl)ethylcarbamoyl)-2-methylpyridin-3-yl)-6-(1-methyl-1H-pyrazol-4-yl)pyrazolo[1,5-a]pyridine-3-carboxamide L-tartrate crystals and left to stir at 28° C. for 55 h. The suspension was filtered and washed with methanol (5 ml). The isolated solid material was dried in a vacuum oven at room temperature for 48 h to yield the title product.

XRPD

| Angle 2-Theta °<br>+/− 0.2° 2theta | d value Angstrom | Intensity % |
|---|---|---|
| 4.4 | 20.01182 | 54 |
| 7.7 | 11.42206 | 42 |
| 8.9 | 9.93644 | 25 |
| 9.7 | 9.06848 | 7 |
| 10.1 | 8.74965 | 18 |
| 13.1 | 6.73932 | 15 |
| 13.6 | 6.48990 | 18 |
| 14.8 | 5.99838 | 35 |
| 15.1 | 5.87831 | 76 |
| 15.7 | 5.64216 | 20 |
| 16.2 | 5.46062 | 36 |
| 16.4 | 5.38720 | 32 |
| 17.0 | 5.20593 | 86 |
| 17.6 | 5.04867 | 47 |
| 17.8 | 4.96741 | 26 |
| 18.7 | 4.75089 | 28 |
| 19.6 | 4.52384 | 29 |
| 20.0 | 4.42756 | 34 |
| 20.3 | 4.36630 | 32 |
| 21.4 | 4.14986 | 57 |
| 21.9 | 4.06241 | 54 |
| 22.1 | 4.01221 | 58 |
| 22.4 | 3.96291 | 34 |
| 22.8 | 3.90483 | 30 |
| 23.5 | 3.78384 | 52 |
| 24.2 | 3.67330 | 100 |
| 25.1 | 3.55100 | 21 |
| 25.4 | 3.50847 | 19 |
| 26.0 | 3.42749 | 72 |
| 26.5 | 3.36553 | 27 |
| 26.9 | 3.31438 | 19 |
| 27.4 | 3.25825 | 31 |
| 28.0 | 3.18592 | 18 |
| 28.6 | 3.11588 | 13 |
| 29.2 | 3.05636 | 13 |
| 29.6 | 3.01628 | 17 |
| 30.0 | 2.97804 | 18 |
| 30.4 | 2.93452 | 26 |
| 30.8 | 2.90263 | 17 |
| 31.5 | 2.83906 | 16 |
| 32.2 | 2.77944 | 11 |
| 32.8 | 2.73016 | 13 |
| 33.3 | 2.68860 | 22 |
| 34.2 | 2.62044 | 13 |
| 34.5 | 2.59784 | 23 |
| 35.0 | 2.56176 | 9 |
| 35.6 | 2.52045 | 12 |
| 36.3 | 2.47133 | 18 |
| 37.0 | 2.42662 | 18 |
| 37.6 | 2.39307 | 16 |
| 38.0 | 2.36408 | 17 |
| 38.7 | 2.32391 | 18 |

DSC

Differential Scanning Calorimetry (DSC) Data

The DSC curve shows two thermal events. The first endotherm with an onset temperature of 49.4° C. is likely attributable to the evaporation of residual solvent in the sample and may not be reproducible with other samples. The second endotherm with an onset temperature of 213.2° C. is related to the melting of the sample and subsequent decomposition.

Example 6

Complex of N-(5-(2-(2,2-dimethylpyrrolidin-1-yl) ethylcarbamoyl)-2-methylpyridin-3-yl)-6-(1-methyl-1H-pyrazol-4-yl)pyrazolo[1,5-a]pyridine-3-carboxamide and Saccharin 100 mg of N-(5-(2-(2,2-dimethylpyrrolidin-1-yl)ethylcarbamoyl)-2-methylpyridin-3-yl)-6-(1-methyl-1H-pyrazol-4-yl)pyrazolo[1,5-a]pyridine-3-carboxamide (free base) was dissolved in 1100 μL of IPA at 55° C., 1000 μL of 0.2M saccharin in IPA was added in drops at 1:1 molar ratio. This resulting suspension was heated at 55° C. and stirred for 60 minutes. The suspension was cooled at approximately 0.3° C./min to 5° C. where it was held for 60 minutes. Cycle was repeated 3 times. The heating rate to 55° C. was 1° C./min and finally hold at 5° C. The resulting solid was collected by filtration and dried at 40° C. under vacuum for about 4 hours.

Alternatively, a suspension of N-(5-(2-(2,2-dimethylpyrrolidin-1-yl)ethylcarbamoyl)-2-methylpyridin-3-yl)-6-(1-methyl-1H-pyrazol-4-yl)pyrazolo[1,5-a]pyridine-3-carboxamide saccharinate in methanol or water or acetone/water was shaken at 25° C. or 50° C. for 5 days and the resulting solid collected by filtration.

XRPD

| Angle 2-Theta ° +/- 0.2° 2theta | d value Angstrom | Intensity % |
| --- | --- | --- |
| 5.1 | 17.35812 | 3 |
| 6.7 | 13.26581 | 33 |
| 7.1 | 12.37341 | 4 |
| 8.4 | 10.49365 | 25 |
| 10.2 | 8.64962 | 7 |
| 12.3 | 7.18097 | 20 |
| 13.4 | 6.58932 | 91 |
| 13.7 | 6.46430 | 100 |
| 14.4 | 6.14246 | 74 |
| 15.1 | 5.87078 | 6 |
| 15.5 | 5.69675 | 35 |
| 16.0 | 5.53466 | 6 |
| 16.7 | 5.29408 | 10 |
| 17.2 | 5.16567 | 16 |
| 17.8 | 4.97060 | 4 |
| 18.4 | 4.82574 | 19 |
| 18.7 | 4.74423 | 6 |
| 19.3 | 4.58953 | 19 |
| 19.9 | 4.46403 | 6 |
| 20.3 | 4.37907 | 13 |
| 20.8 | 4.25856 | 11 |
| 21.2 | 4.19023 | 28 |
| 21.7 | 4.08851 | 24 |
| 22.5 | 3.94724 | 13 |
| 22.7 | 3.90869 | 16 |
| 23.5 | 3.78515 | 7 |
| 24.1 | 3.68513 | 8 |
| 24.4 | 3.64974 | 8 |
| 25.1 | 3.54934 | 41 |
| 25.6 | 3.47926 | 20 |
| 26.0 | 3.42684 | 33 |
| 26.9 | 3.30877 | 12 |
| 27.3 | 3.26202 | 11 |
| 27.7 | 3.21928 | 13 |
| 28.1 | 3.17698 | 11 |
| 28.3 | 3.15023 | 17 |
| 29.1 | 3.06344 | 9 |
| 29.5 | 3.02534 | 9 |

DSC

Differential Scanning Calorimetry (DSC) Data

The DSC curve shows an endotherm with an onset temperature of 266.1° C. which is related to the melting of the sample (melting endotherm).

Preparation of Intermediates

Intermediate 1

7-Bromoimidazo[1,2-a]pyridine-3-carboxylic acid

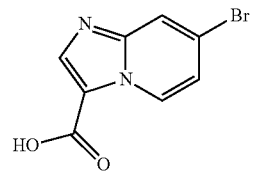 [SMILES: O=C(O)c1cnc2cc(Br)ccn12]

Step 1: Potassium (Z)-2-chloro-1-ethoxy-3-oxoprop-1-en-1-olate

A cooled (0° C.) suspension of ethyl 2-chloroacetate (17.47 ml, 163 mmol) and ethyl formate (13.18 ml, 163 mmol) in ether (250 ml) was treated slowly (over 3 hrs) with potassium 2-methylpropan-2-olate (18.31 g, 163 mmol) keeping the temperature below 5° C. The mixture was concentrated in vacuo and the resulting solid was washed with ether and dried (47° C. in a vacuum oven) to afford the title compound;

1H NMR (400 MHz, d6-DMSO) δ 8.95 (1H, s), 3.9 (2H, q), 1.1 (3H, t).

Step 2: Ethyl 7-bromoimidazo[1,2-a]pyridine-3-carboxylate

A solution of 4-bromopyridin-2-amine (10 g, 57.8 mmol) and potassium (Z)-2-chloro-1-ethoxy-3-oxoprop-1-en-1-olate (step 1) (23.4 g, 124 mmol) in ethanol (200 ml) was cooled to 5° C. Sulfuric acid (7.70 ml, 144 mmol) was added dropwise and the reaction heated to reflux at 90° C. for 3 hrs. The mixture was cooled to RT and TEA (20.03 ml, 144 mmol) was slowly added and heating continued at 90° C. for 18 hrs. After cooling to RT, the mixture was filtered and the solid was partitioned between EtOAc and aqueous 2M HCl. The aqueous layer was basified (NaOH, solid pellets) and extracted using EtOAc. The combined organic extracts were dried (MgSO$_4$) and concentrated in vacuo to afford the title compound;

1H NMR (400 MHz, d6-DMSO) δ 9.1 (1H, d), 8.3 (1H, s), 8.2 (1H, s), 7.4 (1H, d), 4.4 (2H, q), 1.4 (3H, t)

Step 3: 7-Bromoimidazo[1,2-a]pyridine-3-carboxylic acid

Ethyl 7-bromoimidazo[1,2-a]pyridine-3-carboxylate (step 2) (30.81 g, 114 mmol) in MeOH (172 ml) was treated with 2M NaOH (172 ml, 343 mmol) and the mixture was heated to 60° C. for 40 minutes. The volatile solvent was removed in vacuo and the crude material was treated with 2M sodium bisulfate solution to adjust the pH to 6-7. The resulting solid was collected by filtration and added to water (400 ml). The mixture was stirred and heated to 90° C. for 1 h. After cooling to RT, the suspension was filtered and dried in a vacuum over at 40° C. to afford the title product;

LC-MS: Rt 0.59 mins; MS m/z 243.1 {M+H}+; Method 2 min LC_v003

Intermediate 2

Methyl 5-amino-6-methylnicotinate

Step 1: Methyl 2-chloro-6-methyl-5-nitronicotinate

To a suspension of 6-methyl-5-nitro-2-oxo-1,2-dihydropyridine-3-carboxylic acid (commercially available) (12.5 g, 63.1 mmol) in chlorobenzene (210 ml) was added DMF (2.442 ml, 31.5 mmol) followed by $POCl_3$ (23.52 ml, 252 mmol). The mixture was heated at 133° C. for 1 hr. After cooling to RT, the mixture was concentrated in vacuo. The residue was cooled in an ice bath, treated with MeOH (200 ml, 4944 mmol) and stirred at RT for 16 hrs. The mixture was concentrated in vacuo and the residue was partitioned between water (300 ml) and EtOAc (300 ml). The organics were dried ($MgSO_4$) and concentrated in vacuo to afford the title compound as a red crystalline solid;

LC-MS: Rt 1.10 mins; MS m/z 230.9 {M+H}+; Method 2 min LC_v003

Step 2: Methyl 5-amino-6-methylnicotinate

Methyl 2-chloro-6-methyl-5-nitronicotinate (step 1) (6.9 g, 29.9 mmol) was added to a suspension of ammonium formate (18.87 g, 299 mmol) and 10% Pd (Carbon) (0.522 g, 0.491 mmol) in MeOH (330 ml) and the mixture was heated at reflux for 3 hrs. After cooling to RT, the mixture was filtered through Celite® (filter material) and washed through with MeOH. The solvent was removed in vacuo and the crude product was triturated with EtOAc to give an orange solid. Purification by chromatography on silica eluting with 0-100% EtOAc in iso-hexane afforded the title product.

Intermediate 3

7-Bromo-N-(5-(2-(2,6-cis-dimethylpiperidin-1-yl)ethylcarbamoyl)-2-fluorophenyl)imidazo[1,2-a]pyridine-3-carboxamide

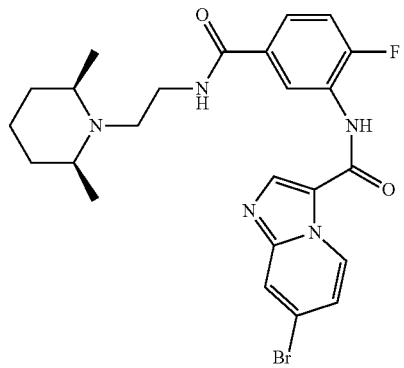 [SMILES: C[C@@H]1CCC[C@H](C)N1CCNC(=O)c1ccc(F)c(NC(=O)c2cnc3cc(Br)ccn23)c1]

Step 1: 3-Amino-N-(2-(2,6-cis-dimethylpiperidin-1-yl)ethyl)-4-fluorobenzamide

A mixture comprising 2-(2,6-cis-dimethylpiperidin-1-yl)ethanaminium chloride (4 g, 20.75 mmol) and methyl 3-amino-4-fluorobenzoate (3.51 g, 20.75 mmol) in THF (50 ml) was treated with TBD (2.89 g, 20.75 mmol) and stirred at 80° C. for 16 hrs. A further portion of methyl 3-amino-4-fluoro benzoate (1 g) and TBD (0.5 g) were added and heating continued for 24 hrs. The resulting mixture was partitioned between ethyl acetate and aqueous sodium bicarbonate. The mixture was extracted once with ethyl acetate and once with chloroform. The combined organic layers were dried ($MgSO_4$), filtered and evaporated to dryness. Purification of the residue by chromatography on silica eluting with 0-20% MeOH in DCM afforded the title compound;

LC-MS: Rt 0.71 mins; MS m/z 294 {M+H}+; Method 2 min LC_v003.

Step 2: 7-Bromo-N-(5-(2-(2,6-cis-dimethylpiperidin-1-yl)ethylcarbamoyl)-2-fluorophenyl)imidazo[1,2-a]pyridine-3-carboxamide 7-Bromoimidazo[1,2-a]pyridine-3-carboxylic acid (Intermediate 1) (1.150 g, 4.77 mmol) was suspended in toluene (10 ml) and treated with thionyl chloride (1.045 ml, 14.32 mmol). The mixture was at 100° C. for 2 hrs. The solvent was removed in vacuo and the solid was added to a stirred solution of 3-amino-N-(2-(2,6-cis-dimethyl piperidin-1-yl)ethyl)-4-fluorobenzamide (1.4 g, 4.77 mmol) in dry pyridine (5 ml) containing oven dried molecular sieves. The mixture was stirred at RT under nitrogen atmosphere overnight. The solvent was removed in vacuo and purification of the crude product by chromatography on silica eluting with 0-20% MeOH in DCM afforded the title compound;

LC-MS: Rt 0.82 mins; MS m/z 516{M+H}+; Method 2 min LC_v003

The invention claimed is:

1. A crystalline form of N-(5-(2-(2,2-dimethylpyrrolidin-1-yl)ethylcarbamoyl)-2-methylpyridin-3-yl)-6-(1-methyl-1H-pyrazol-4-yl)pyrazolo[1,5-a]pyridine-3-carboxamide saccharinate.

2. The crystalline form according to claim 1, characterized by a X-ray powder diffraction pattern comprising four or more 2Θ values chosen from 13.4±0.2°, 13.7±0.2°, 14.4±0.2°, 15.5±0.2°, 25.1±0.2° and 26.0±0.2° when measured at a temperature of about 25° C.

3. The crystalline form according to claim 1, characterized by a X-ray powder diffraction pattern comprising five or more 2Θ values chosen from 6.7±0.2°, 8.4±0.2°, 12.3±0.2°, 13.4±0.2°, 13.7±0.2°, 14.4±0.2°, 15.5±0.2°, 21.2±0.2°, 21.7±0.2°, 25.1±0.2°, 25.6±0.2° and 26.0±0.2° when measured at a temperature of about 25° C.

4. A pharmaceutical composition comprising a crystalline form of N-(5-(2-(2,2-dimethylpyrrolidin-1-yl)ethylcarbamoyl)-2-methylpyridin-3-yl)-6-(1-methyl-1H-pyrazol-4-yl)pyrazolo[1,5-a]pyridine-3-carboxamide saccharinate and one or more pharmaceutically acceptable carriers.

5. A pharmaceutical composition according to claim 4, wherein the composition further comprises one or more additional therapeutically active agents.

6. A method of treating a respiratory disorder or disease mediated by the PDGF receptor in a subject in need thereof, comprising administering to the subject in need thereof a crystalline form of N-(5-(2-(2,2-dimethylpyrrolidin-1-yl)ethylcarbamoyl)-2-methylpyridin-3-yl)-6-(1-methyl-1H-pyrazol-4-yl)pyrazolo[1,5-a]pyridine-3-carboxamide saccharinate, wherein the respiratory disorder or disease is chosen from asthma, allergic rhinitis, pulmonary arterial hypertension (PAH), and pulmonary fibrosis.

7. The method according to claim 6 wherein the respiratory disorder or disease is pulmonary arterial hypertension (PAH).

8. The method according to claim 6 wherein the respiratory disorder or disease is asthma.

9. The method according to claim 6 further comprising one or more additional therapeutically active agents.

10. The compound N-(5-(2-(2,2-dimethylpyrrolidin-1-yl)ethylcarbamoyl)-2-methylpyridin-3-yl)-6-(1-methyl-1H-pyrazol-4-yl)pyrazolo[1,5-a]pyridine-3-carboxamide saccharinate.

11. A pharmaceutical composition comprising N-(5-(2-(2,2-dimethylpyrrolidin-1-yl)ethylcarbamoyl)-2-methylpyridin-3-yl)-6-(1-methyl-1H-pyrazol-4-yl)pyrazolo[1,5-a]pyridine-3-carboxamide saccharinate and one or more pharmaceutically acceptable carriers.

12. A pharmaceutical composition according to claim 11, wherein the composition further comprises one or more additional therapeutically active agents.

13. A method of treating a respiratory disorder or disease mediated by the PDGF receptor in a subject in need thereof, comprising administering N-(5-(2-(2,2-dimethylpyrrolidin-1-yl)ethylcarbamoyl)-2-methylpyridin-3-yl)-6-(1-methyl-1H-pyrazol-4-yl)pyrazolo[1,5-a]pyridine-3-carboxamide saccharinate to the subject in need thereof, wherein the respiratory disorder or disease is chosen from asthma, allergic rhinitis, pulmonary arterial hypertension (PAH), and pulmonary fibrosis.

14. The method according to claim 13 wherein the respiratory disorder or disease is pulmonary arterial hypertension (PAH).

15. The method according to claim 13 wherein the respiratory disorder or disease is asthma.

16. The method according to claim 13 further comprising one or more additional therapeutically active agents.

17. The pharmaceutical composition according to claim 4 wherein the crystalline form is characterized by a X-ray powder diffraction pattern comprising four or more 2Θ values chosen from 13.4±0.2°, 13.7±0.2°, 14.4±0.2°, 15.5±0.2°, 25.1±0.2° and 26.0±0.2°.

\* \* \* \* \*